(12) United States Patent
Clack et al.

(10) Patent No.: US 7,423,136 B2
(45) Date of Patent: Sep. 9, 2008

(54) NUCLEIC ACID FOR BIOTIN PRODUCTION

(75) Inventors: Beatrice A. Clack, Nacogdoches, TX (US); Alan B. Youngblood, Nacogdoches, TX (US)

(73) Assignee: Stephen F. Austin State University, Nacagdoches, TX (US)

( * ) Notice: Subject to any disclaimer, the term of this patent is extended or adjusted under 35 U.S.C. 154(b) by 14 days.

(21) Appl. No.: 11/252,546

(22) Filed: Oct. 19, 2005

(65) Prior Publication Data

US 2007/0087419 A1   Apr. 19, 2007

(51) Int. Cl.
C07H 21/02 (2006.01)
C12N 15/00 (2006.01)
C12P 1/00 (2006.01)

(52) U.S. Cl. .................. 536/23.1; 435/320.1; 435/41

(58) Field of Classification Search .............. None
See application file for complete search history.

(56) References Cited

U.S. PATENT DOCUMENTS

| 3,859,167 A | 1/1975 | Ogino et al. |
| 6,656,721 B1 | 12/2003 | Hohmann et al. |
| 6,841,366 B1 | 1/2005 | Bower et al. |
| 6,955,906 B2 | 10/2005 | Furuichi |

*Primary Examiner*—Kathleen Kerr Bragdon
*Assistant Examiner*—Alexander D Kim
(74) *Attorney, Agent, or Firm*—Gardere Wynne Sewell, LLP; Scott C. Sample

(57) ABSTRACT

The present invention relates to the production process of biotin by fermentation using genetically engineered microorganisms, including *Escherichia coli* and *Pseudomonas mutabilis*, and DNA sequences and vectors to be used in such process.

24 Claims, 15 Drawing Sheets 3 of 15 Biotin Enzyme Activity

NUCLEIC ACID FOR BIOTIN PRODUCTION

GOVERNMENTAL INTEREST

Not applicable.

BACKGROUND OF THE INVENTION

The present invention relates to the production of biotin using genetically engineered organisms.

Biotin (vitamin $B_8$ or vitamin H) is a nonpolypeptide coenzyme molecule involved in enzyme-catalyzed reactions requiring carboxyl group transfers. Biotin, like many coenzymes, cannot be synthesized by animals and must instead be obtained exogenously from plants or microorganisms in the diet. Large-scale production of biotin for commercial use as a dietary supplement is therefore desirable. Genetically-modified microorganisms may produce dietary supplements in commercially advantageous amounts and the present invention provides an approach to accomplish this goal for biotin.

The synthesis of biotin in microorganisms is achieved by both chemical and fermentation methods. At the genetic level, microbial synthesis of biotin in vivo is driven from an operon containing a cluster of genes. The arrangement of genes within the cluster is specific to each bacterial species. Additionally, the concentration of intermediates and product, as well as the amount of biotinylated protein in a cell, regulates biotin operon transcriptional activity (Weaver et al., 2001). For instance, repression of the operon occurs through binding of the birA gene product together with biotinoyl-AMP to the regulatory sequence that lies between the bioA gene and the biotin operon (Weaver et al., 2001; Brown and Kamogawa, 1991).

Biotin synthesis requires the proteins encoded by the bioH, bioC, bioF, bioA, bioD, and bioB genes. (Otsuka A J et al., 1988; Sakurai N et al., 1996; Brown and Kamogawa, 1991; Pollock and Barber, 2001; Picciocchi et al., 2001; Ploux and Marquet, 1992; Gibson et al. 1995). The enzymatic steps involved in the biotin synthetic pathway from pimelic acid to biotin has not been elucidated fully in *Pseudomonas*. Generally, however, as shown in FIG. 1, the steps are predicted to include converting (1) pimelic acid to pimelyl-CoA (PmCoA) by the bioC gene product, which is unidentified, and pimeloyl CoA synthetase that is encoded by bioH (Ploux et al., 1992); (2) Pimelyl-CoA to 7-keto-8-amino pelargonic acid (KAPA) by 7-KAP synthetase (BioF); (3) KAPA to 7,8-diamino-pelargonic acid (DAPA) by DAPA aminotransferase (BioA); (4) DAPA to dethiobiotin by dethiobiotin synthetase (BioD); and (5) dethiobiotin to biotin by biotin synthetase (BioB). See FIG. 1. Synthesis of PmCoA reportedly involves different enzymatic steps in different microorganisms. (Bower et al., 1996)

The biotin operon for *E. coli* consists of a 5.8 Kb region containing five biotin operon genes, bioA, bioB, bioF, bioC and bioD (Otsuka et al., 1988). The bioA gene runs in the opposite direction with control of the operon being between the bioA and bioB sequences, basepairs 807,191 through 812,170 for *E. coli* K12 (NCBI accession number: NC_000913). The regulatory region is shared by bioA and the rest of the cassette having two promoters running in the opposite direction and on either side of the operator (Brown and Kamogawa, 1991). BioH, in *E. coli*, is located several kilobases downstream from the operon starting at nucleotide 3,542,096. This gene arrangement for the biotin operon is similar in *Serratia marcescens* (Sakurai et al., 1996). In *Bacillus subtilis*, the arrangement is W(H)AFDBIorf2 (Bower et al., 1996). Similarly, *Pseudomonas aeruginosa* has the bioH as part of the biotin operon but it is unknown whether *mutabilis* similarly does. Additionally, the bioA gene in *P. aeruginosa* is further away from the biotin BFHCD operon by close to 100 Kb but within the operon for *B. subtilis*. Although similar gene products are necessary for synthesis of biotin in these different bacteria, the arrangement of the genes encoding the necessary proteins varies from genus to genus. (Rodionov et al., 2002)

Previously genetically modified microorganisms have suffered from poor conversion of dethiobiotin to biotin, inefficient promoters, poor gene cluster arrangements and unsatisfactory biotin production. The present invention overcomes these deficiencies through the combination of specific genes whose encoded products are involved in biotin synthesis. Furthermore, the present invention discloses the creation of a mutant strain of *Pseudomonas mutabilis* that produces gram per liter amounts of biotin when transformed with a unique synthetic operon engineered according to the teachings disclosed herein.

SUMMARY OF THE INVENTION

The present invention relates to biotin biosynthesis in transformed *Pseudomonas mutabilis* and *Escherichia coli*. Chromosomal DNA fragments carrying biotin biosynthetic genes responsible for biotin biosynthesis were cloned and engineered to increase biotin production, in part, through the unique use of uniquely applied promoter sequences.

The present invention further relates to *Pseudomonas* strains in which at least one gene involved in biotin biosynthesis is reoriented from its natural 5'-3' orientation, and also to the production process of biotin by this genetically engineered *P. mutabilis* strain.

Although the DNA fragments mentioned above may be of various origins, it is preferable to use the strains belonging to the genus *Pseudomonas* and in particular, *P. aeruginosa*.

BRIEF DESCRIPTION OF THE DRAWINGS

A more particular description of the invention, briefly summarized above, may be had by reference to the embodiments thereof which are illustrated in the appended drawings and described herein. It is to be noted, however, that the appended drawings illustrate only some embodiments of the invention and are therefore not to be considered limiting of its scope, because the invention may admit to other equally effective embodiments.

FIG. 3 shows the p519gfp plasmid structures used according to embodiments of the present invention with restriction sites identified.

FIG. 8 is the plasmid structure with insertion of the bioBF-HCD cassette annealed into the pET-30 EK/LIC plasmid with restriction sites identified.

DETAILED DESCRIPTION OF THE PREFERRED EMBODIMENTS

Figure 1:
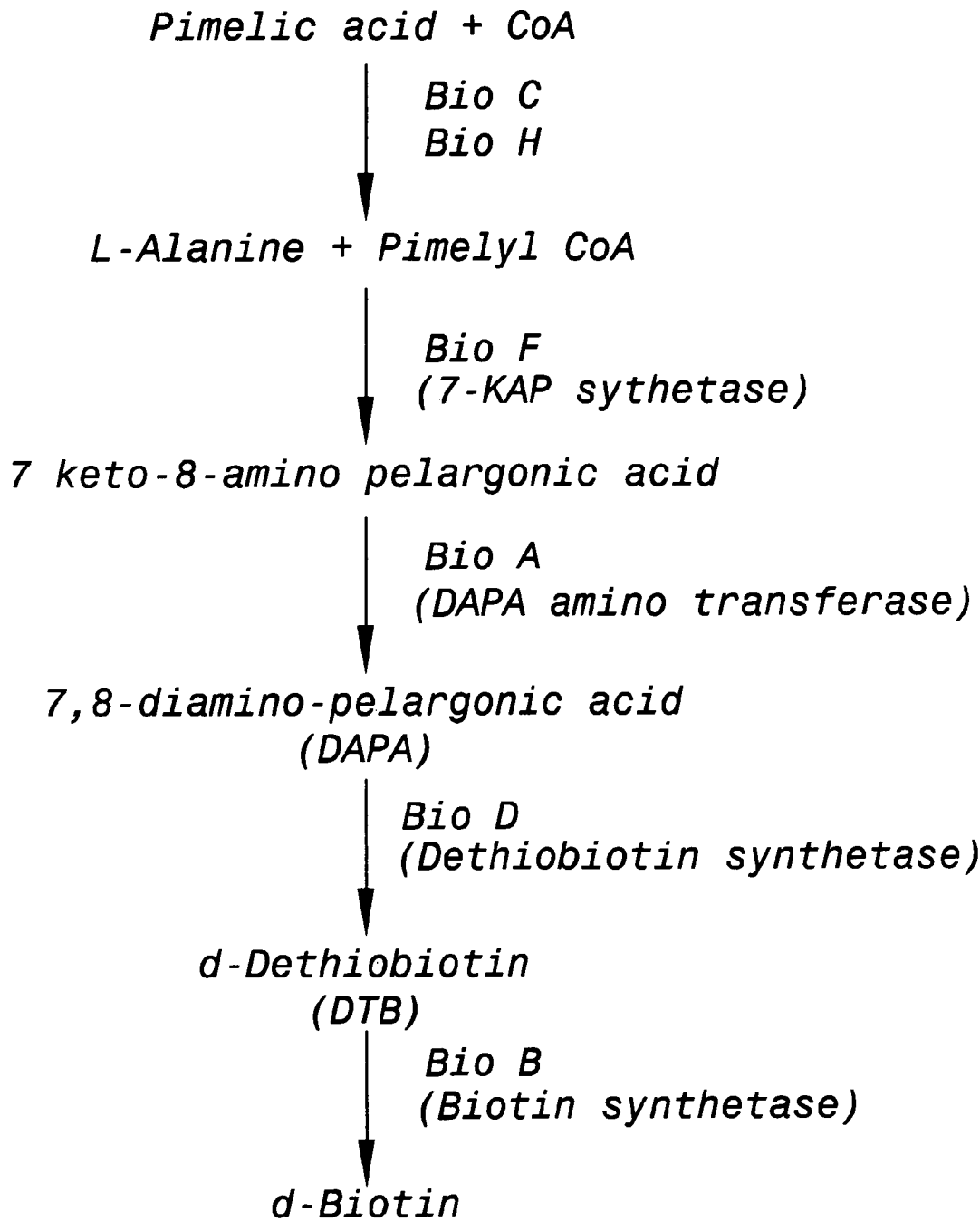
FIG. 1 is the biotin biosynthetic pathway predicted in *Pseudomonas*, including *P. mutabilis*.

The present invention provides a novel genetic construct that comprises a unique arrangement of the complete collection of genes that express proteins necessary for biotin synthesis in *Pseudomonas*. Bacteriophage Pf1 promoters that natively drive expression of coat proteins or drives transcription of other viral proteins were cloned and operably linked to the biotin construct to create a unique operon that overproduces biotin in *P. mutabilis*.

*Pseudomonas* produces biotin and biotin production is self controlled via a negative feedback mechanism. To prevent downregulation of biotin synthesis by biotin itself, *P. mutabilis* mutants were created that constitutively produce biotin. Biotin genes bioB, bioF, bioH, bioC, and bioD were cloned from *P. aeruginosa* as a single primary cassette. BioA is normally found in the reverse direction but 5-prime to the bioBFHCD cluster, but in the practice of the present invention, was reoriented in the same direction but maintained upstream 5-prime to the bioBFHCD cluster, or primary cassette. The bioABFHCD cassette was inserted under the selected bacteriophage promoter cloned previously to form a complete cassette and transformed into the *P. mutabilis* mutant, resulting in the profound overproduction of biotin and highly efficient conversion of dethiobiotin to biotin.

Definitions

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear or linearized DNA" denotes non-circular DNA molecules having free 5' and 3' ends. Linear DNA can be prepared from closed circular DNA molecules, such as plasmids, by enzymatic digestion or physical disruption.

"Primers" as used herein can be RNA or DNA. DNA can be either cDNA or genomic DNA. Polynucleotide probes and primers are single or double-stranded DNA or RNA, generally synthetic oligonucleotides, but may be generated from cloned cDNA or genomic sequences or its complements. Analytical probes will generally be at least 20 nucleotides in length, although somewhat shorter probes (14-17 nucleotides) can be used. PCR primers are at least 5 nucleotides in length, preferably 15 or more nucleotides, more preferably 20-30. Short polynucleotides can be used when a small region of the gene is targeted for analysis.

"Promoter" refers to a nucleotide sequence comprising a regulatory element that drives gene expression, for example, in an expression vector. Several types of promoters are now well known in the transformation arts, as are other regulatory elements that can be used alone or in combination with promoters. If a promoter is an inducible promoter, then the rate of transcription increases in response to an inducing agent. In contrast, the rate of transcription is not regulated by an inducing agent if the promoter is a constitutive promoter. Repressible promoters are also known.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" or "host cell" is a cell that contains a heterologous nucleic acid molecule, such as a cloning vector or expression vector. In the present context, an example of a recombinant host is a cell from *E. coli* or *Pseudomonas* that produces biotin biosynthetic enzymes from an expression vector. In contrast, biotin biosynthetic enzymes can be produced by a cell that is a "natural source" of biotin biosynthetic enzymes, and that lacks an expression vector.

Production of *Pseudomonas mutabilis* Mutant

Mutagenesis of *Pseudomonas mutabilis*.

To circumvent the negative feedback loop induced by biotin produced from *P. mutabilis* itself, mutants that could no longer turn off biotin synthesis or no longer downregulate biotin were created. Mutagenesis was performed on *P. mutabilis* using two methods designated "acute" and "chronic". Buffers utilized were 0.01 M potassium phosphate and 0.01 M potassium phosphate with 1.0 mg/mL n-methyl-N'-nitro-N-nitrosoguanidine (nitrosoguanidine) as a mutagenic agent.

Acute Mutagenesis

*P. mutabilis* was grown in 1.0 L of Difco 0001 media 48 hours in a 37° C. shaker incubator at 200 rpm. Eight 50 mL conical tubes with 50 mL of culture were collected and centrifuged at 3000 rpm for 20 minutes to compact cells and 100 mLs of culture was reserved for later use. The centrifuged cells were resuspended in 25 mL of 0.01 M potassium phosphate buffer then centrifuged for an additional 20 minutes at 3000 rpm. The supernatant was discarded and the cells were washed twice with buffer and then resuspended in 10 mL of 0.01 M potassium phosphate buffer containing 0.1 mg/mL of nitrosoguanidine. The cells were gently resuspended and allowed to incubate for 15 minutes in a 37° C. water bath without shaking. After incubation the cells were centrifuged as before, the supernatant was removed and stored for disposal. The cells were washed twice as before with 0.01 M potassium phosphate buffer. The pelleted cells were then resuspended in 10 mL of Difco 0001 media containing 20% glycerol and transferred to cryotubes in 1.0 mL aliquots, snap frozen in liquid nitrogen, and stored at −70° C. for later use. One tube was stored at −20° C. for immediate use.

Chronic Mutagenesis

Difco 0001 media (600 mL), containing 0.01 mg/mL of nitrosoguanidine was added to the reserved culture (100 mL). This culture was allowed to grow for 50 hours in a 37° C. shaker incubator at 200 rpm. Cells were processed as with acute mutagenesis protocol with nitrosoguanidine except, due to high cell density, 30 mL of cryobuffer was used for final resuspension. Cells were aliquoted at 2 mL per cryotube, snap frozen in liquid nitrogen, and stored at −70° C.

In addition to nitrosoguanidine, ethidium bromide (EtBr) was separately used to generate chronic mutants. One milliliter of previously produced chronic mutant *p. mutabilis* culture was added to 500 mL of Difco 0001 media. The culture was allowed to grow until turbid and EtBr was added to a concentration of 10 μg/mL. The culture was exposed to UV light at 336 nm for 5 hours and then allowed to grow overnight at 37° C. as previous. The cells were harvested and stored.

Mutant Selection

Acute Mutant Selection

BM-1 agar plates were prepared and allowed to dry at 37° C. To each plate 200 μL (100 μg/mL) of each of four biotin analogues was applied. The analogue application was allowed to soak into the media for four hours at room temperature protected from light. A $10^{-2}$ dilution (100 μL) of acute mutagenic cells of *P. mutabilis* (previously prepared) was spread onto each plate for a total of ten plates for each of the four biotin analogues: biotin methyl ester, biotin p-nitrophenyl, 4-amido-benzoic acid, and diamino biotin. These plates were incubated overnight at 28° C. Cells were plated onto BM-1 plates without analogues as a control. Sparse to no growth was observed. This protocol was repeated until a sizeable number of colonies were collected for each analogue. A total 17, 17, 14 and 10 colonies were collected for biotin analogues biotin methyl ester, biotin p-nitrophenyl, 4-amido-benzoic acid, and diamino biotin, respectively. Each of the picked colonies was placed into 3.0 mL of sterile M-1 media in a 5.0 mL snap-top culture tube and allowed to grow overnight at –37° C. in a shaker incubator at 250 rpm. A sample of 1.5 mL was taken the next day and was exposed to three cycles of freeze-thawing using liquid nitrogen and centrifuged to compact cell debris. The supernatant was removed and stored at –20° C. until needed to determine which mutant resulted in constitutive biotin production.

Selection of Chronic Mutant Selection

A similar procedure was used to select the chronic mutants with the exception that selection was against 1000 μg/mL of each analogue per plate. Because of a high cell density, a $10^{12}$ dilution was prepared and plated at 100 μL per plate. Seventy-two colonies were selected for each analogue. The colonies were grown overnight and supernatant was prepared as with the acute mutants. The chronic EtBr mutants were also selected. Seventy-two colonies were selected for subsequent screening on each analogue.

Mutant colonies were screened for maximum production of biotin in the presence of the analogue by the use of 4-Hydroxyazobenzene-2-carboxylic acid (HABA). Briefly, HABA/Avidin is used to determine biotin concentrations. HABA dye is bound to avidin initially. Avidin has a greater affinity for biotin than it has for HABA. As a result, as biotin binds avidin, the amount of free HABA becomes greater in the presence of biotin. Unbound (free) HABA, which reflects the amount of biotin that is present, is measured by the change in its absorbance at 500 nm ($Abs_{500}$). HABA was obtained from Sigma/Aldrich and the protocol was followed according to the information provided. (Sigma/Aldrich, Product No. H2153 referencing Green N M, 1970). The range in $Abs_{500}$ change is between 0.1-0.4. A scaled down reaction was utilized on a 96 well microtiter plate. In each case 10 μL of previously prepared and stored supernatant was added to 90 μL of HABA/Avidin reagent. Phosphate-buffered saline (PBS) 1× was used as a diluent. For each of the 96 well plates, triplicate biotin standards were applied. The standards were applied in the following gradient: 1.0 μg/mL, 2.5 μg/mL, 5.0 μg/mL, 10 μg/mL, 25 μg/mL, and 50 μg/mL. In addition, triplicate samples of HABA only and HABA plus 10 μL of M1 media only were used as blanks and background, respectively.

Preparation of Primary Plasmid for Expression of Bio Genes

Restriction Digestion of the p519gfp Plasmid

Figure 2:
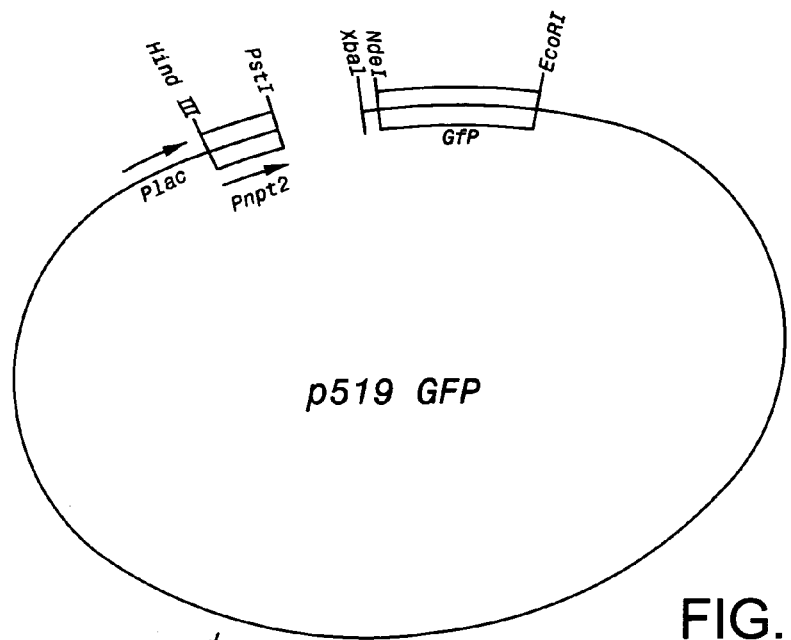
FIG. 2 is the plasmid structure for the p519gfp plasmid used to assess Pf1 phage promoter strength and that served as the foundation plasmid in embodiments of the present invention.

The p519gfp plasmid served as the foundation plasmid using green fluorescent protein (GFP) to report promoter strength (ATCC 87453; Matthysse et al, 1996). The GFP gene was excised from the final construct. The p519gfp plasmid in host bacteria was obtained from the American Type Culture Collection, Accession No. 87452 (lot 1178894) (P.O. Box 1549, Manassas, Va. 20108). The structure of the p519gfp plasmid is shown in FIG. 2. XbaI and EcoRI restriction sites border the GFP gene within the p519gfp plasmid. XbaI and EcoRI were used to replace the GFP gene with the biotin cassette, discussed below. The lyophilized p519gfp plasmid was resuspended in 500 μL of phosphate-buffered saline (PBS) containing 20% glycerol. The suspension was aliquoted (50 μL), snap frozen in liquid nitrogen, and stored at –70° C. for later use. One tube was used to make dilutions and plated onto LB plated containing 50 μg/mL of kanamycin (Kan). Proper insertion of the promoter sequence conveys kanamycin resistance of the host cell. These plates were placed into a 37° C. incubator overnight. One colony from these plates was selected and grown overnight in 300 mL of LB/50 μg/mL of Kan and 150 mLs of the overnight culture was used for plasmid DNA purification using Qiagen Miniprep protocols (Qiagen, Inc., 27220 Turnberry Lane, Suite 200, Valencia, Calif. 91355). The DNA was stored at –20° C. in TRIS buffer. The residual 150 mL of cells were centrifuged, resuspended in PBS 20% glycerol, snap frozen, and stored at –70° C.

Preparation of Bacteriophage Pf1 Promoters

Synthesis of Bacteriophage Promoters

Filamentous bacteriophages such as Pf1, Pf3, fd, M13, Xf1/If1 and Ike produce thousands of copies of G8 coat protein that form a protein capsid surrounding a single copy of single-stranded circular DNA, and each of the DNAs for these viral phages contains an intergenic region (IR) responsible for replication and transcription of other viral proteins. The promoters in these viruses are thus strong promoters due to the number of proteins that must be generated and for this reason were used in the design of this expression system. The use of these promoters in expression of recombinant proteins is a novel concept for the present invention. Bacteriophage Pf1 was selected for its ability to infect *Pseudomonas* species but one of ordinary skill would recognize that Pf3, fd, M13 or Xf1/If1 and other bacteriophage promoters may also be used.

Two promoters derived from bacteriophage Pf1 were prepared, one from the Pf1 intergenic region (IR) and one that drives expression of the Gene-8 protein (G8). A third synthetic promoter was the consensus promoter designed based on the consensus sequence for RNA polymerase which was computer designed.

Figure 3A:
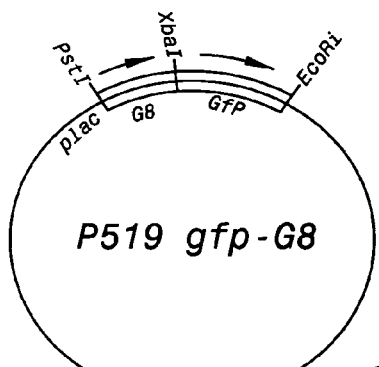
FIG. 3A shows the p519gfp plasmid with the G8 promoter.
Figure 3C:
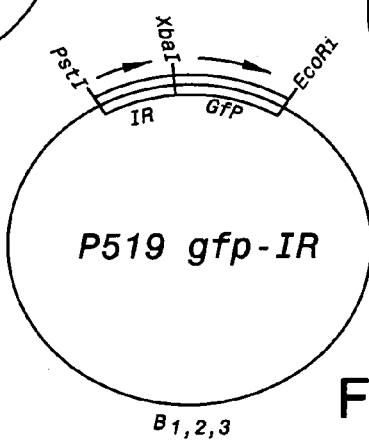
FIG. 3C shows the p519 plasmid with the IR promoter.
Figure 3B:
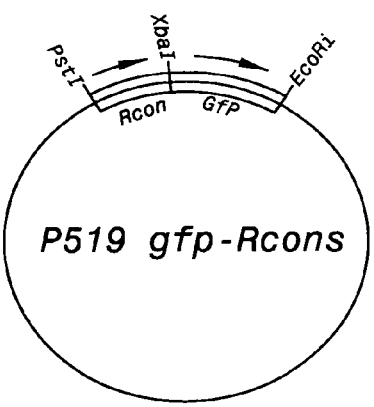
FIG. 3B shows the p519gfp plasmid with the consensus promoter (Rcon).

The consensus promoter was produced by annealing SEQ ID NO: 1 and SEQ ID NO: 2 that were chosen to provide post-annealing PstI and XbaI restriction site overhangs. Ten microliters (20 pmol) of each of the consensus promoter oligonucleotide stock solutions were mixed in a 1.5 mL microfuge tube. The tube was placed into a 95° C. water bath for 5 minutes. A 250 mL beaker was filled with the 95° C. water and the tube added. The beaker containing the tubes with the consensus oligonucleotides of SEQ ID NO: 1 and SEQ ID NO: 2 was then allowed to cool to room temperature. The annealed oligonucleotides comprising SEQ ID NO: 1 and SEQ ID NO: 2 were then directly ligated into the linearized p519gfp plasmid at the PstI/XbaI sites as shown in FIG. 3B. The PstI/XbaI sites were also used for ligation of the G8 and IR promoters, shown in FIG. 3A and FIG. 3C, respectively.

Figure 4:
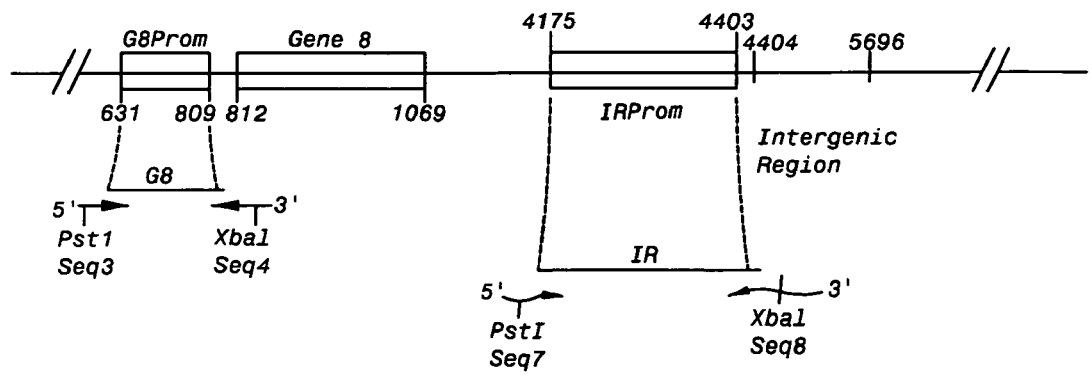
FIG. 4 is a partial-Pf1 chromosomal map showing G8 and IR Pf1 promoters with restriction sites and PCR primer sequences.

Promoters from the Gene-8 protein (G8) and intergenic region (IR) were prepared using standard PCR methods as described in Sambrook and Russell, 2001 and well known to one of ordinary skill. The promoter region for the G8 coat protein of bacteriophage Pf1 was produced via PCR using primers set forth in SEQ ID NO: 3 and SEQ ID NO: 4, as shown in FIG. 4. The G8 promoter sequence is set forth in SEQ ID NO: 5.

Likewise, the IR promoter region, set forth in SEQ ID NO: 6 was also produced via PCR primers set forth in SEQ ID NO: 7 and SEQ ID NO: 8. (See FIG. 4) All oligonucleotides were obtained from Operon Biotechnologies, Inc. (2705 Artie Street Bldg. 400, Ste. 27 Huntsville, Ala. 35805). All oligonucleotides were obtained in a lyophilized state and rehydrated in sterile water to a concentration of 200 pmole/µL and a working concentration of 20 pmole/µL was used for all reactions. The promoter PCR reactions consisted of 25 µL of 2×GC buffer I (TaKaRa Mirus Bio Inc. 505, South Rosa Road, Madison, Wis. 53719, USA), 8 µL of dNTP mix from the TaKaRa kit, 20 pmol of SEQ ID NO:3 and SEQ ID NO:4, 1 µL of Pf1 single-stranded DNA, 1 unit of TAQ Polymerase (Promega Corp., 2800 Woods Hollow Road, Madison Wis. 53711) and water to bring final volume of reaction to 50 µL.

Figure 5:
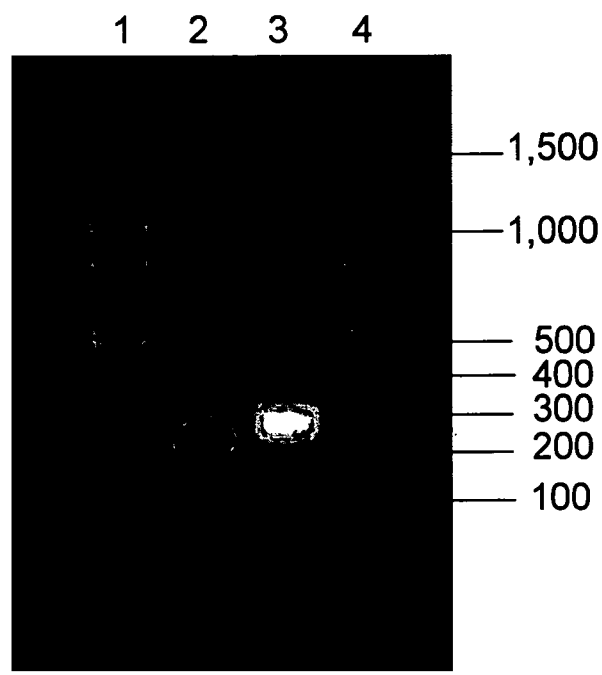
FIG. 5 shows PCR amplification of the Pf1 phage G8 (lane 2) and IR (lane 3) promoter PCR products. Lanes 1 and 4 are 100-bp ladders.

G8 and IR promoters were amplified via PCR. Multiple reactions were set up with varying concentrations of template DNA. The PCR reactions were analyzed by agarose gel electrophoresis as shown in FIG. 5. PCR products at 202 bp and 240 bp correspond to the G8 and IR promoters, respectively. The two respective bands were excised and purified using a Qiagen Gel Extraction kit (Qiagen, Inc., Valencia, Calif.). The PCR products were then digested with XbaI and PstI to prepare them for insertion into the p519gfp plasmid. A separate digest was run for each promoter PCR product. Each digest was incubated overnight in a 37° C. water bath, run on an agarose gel and extracted as before. As shown in FIGS. 3A-3C, the prepared promoters were then ligated into the previously double-digested p519gfp plasmid using T4 DNA ligase (Promega, Corp.). All promoters were ligated in separate reactions. Each ligation mix was transformed into E. coli One-Shot™ (Invitrogen Corp., 1600 Faraday Avenue, P.O. Box 6482, Carlsbad, Calif. 92008) competent cells. The recovered transformation mix was plated onto LB/Kan (50 µg/mL) at a rate of 10 µL, 25 µL, and 50 µL. The plates were incubated overnight at 37° C. Colonies were selected and grown overnight in LB/Kan (50 µg/mL) broth. Kanamycin-resistant cells were used for promoter evaluation.

Promoter Selection

Multiple individual colonies containing the cloned promoter (either G8, IR, or consensus) were picked and individually grown overnight. The strength of the promoter was evaluated as the culture expressing the greatest amount of GFP as detected by fluorescence spectroscopy. Because it produced the highest amount of GFP, the IR promoter sequence set forth in SEQ ID NO: 6 was selected to drive biotin cassette expression. The DNA from these positive promoter constructs was purified. The GFP gene, referred to in FIG. 2, was excised at XbaI and EcoRI and replaced with the biotin gene cassette, as discussed below.

Production of the Expression Cassette

Design and Synthesis of the Expression Cassette

Primers for amplifying the desired biotin genes were designed based on the published sequence of P. aeruginosa (NC_002516). The biotin-related genes have not been reported in P. mutabilis. The primary cassette was designed based on the 5-prime region of bioB and the 3-prime end of bioD. In P. aeruginosa, bioB, bioF, bioH, bioC, and bioD are in a contiguous cluster, or operon, unlike genes of E. coli, B. subtilis and S. marcescens with some other species having bioH separated by several thousand base pairs downstream of the main biotin operon (Otsuka et al. 1988; Brown and Kamogawa, 1991; Sakurai et al. 1996; U.S. Pat. No. 6,656,721; Bower et al. 1996; U.S. Pat. No. 6,057,136). Additionally, bioA is found in the reverse direction 5-prime to the bioBFHCD cluster in P. aeruginosa.

Figure 6:
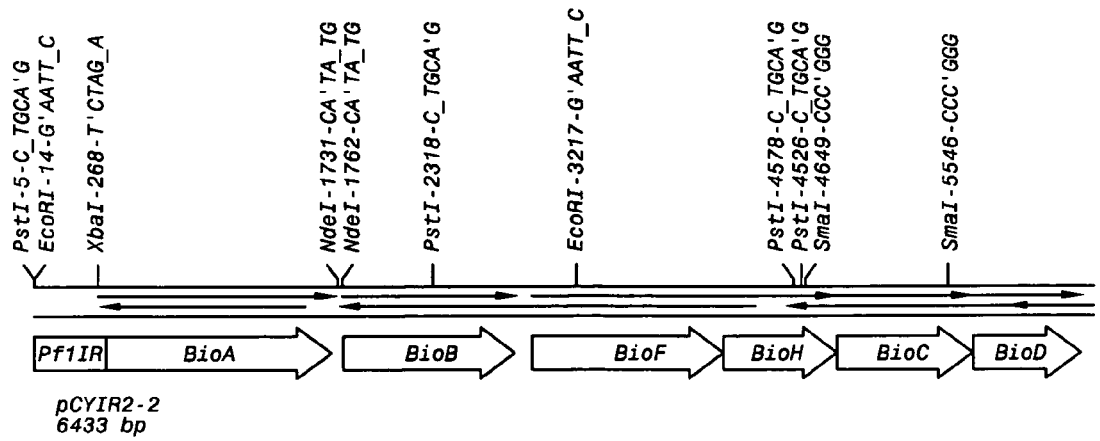
FIG. 6 is a restriction and gene organization map of pCYIR2-2 (6.4 Kb), also referred to as "IR2-2 DNA," of the bio genes according to at least one embodiment of the present invention.

Construction of Complete Biotin Cassette for Both In Vitro and In Vivo Overexpression of Biotin Related Enzymes A novel feature of the present invention is the redirection of the bioA gene necessary for biotin synthesis into the same cassette adjoining genes bioB, bioF, bioH, bioC, and bioD. The restriction map of the complete bioABFHCD cassette is shown in FIG. 6. This amplified product was consistent with the bioBCDHF cluster as the primary cassette with the final addition of the bioA gene moved to the same direction having a separate promoter but same operator, which is normal in the reverse direction. Sequencing and clustering analysis using Lasergene Software (DNASTAR, Inc., 1228 S. Park St., Madison, Wis. 53715) of the amplified cassette product reveals unique DNA provided in SEQ ID NO: 9 created by the novel arrangement of the necessary biotin genes and promoter constructs.

Amplification of the Biotin Gene Cluster bioBFHCD.

The biotin gene cluster cassette was amplified by PCR using primers shown in SEQ ID NO: 10 and SEQ ID NO: 11. The PCR reaction used P. aeruginosa as template genomic DNA set forth in SEQ ID NO: 12 derived from either 1 µL of overnight culture of the P. aeruginosa or from a single colony picked and introduced directly into the PCR reaction tube. Reactions consisted of either: a positive control reaction containing the following reagents supplied from TaKaRa Biologicals comprising 25 µL of 2×GC buffer, 8 µL of dNTP mix, 20 pmol of each control primer GC1 and GC2, TaKaRa Taq, control template, and water to bring final volume to 50 µL; or, the same reaction mixture containing a single colony of P. aeruginosa and primers shown in SEQ ID NO: 10 and SEQ ID NO: 11; or, one microliter of a glycerol stock of P. aeruginosa with primers shown in SEQ ID NO: 10 and SEQ ID NO: 11. Amplification conditions for each reaction were 1 minute at 94° C., 30 cycles of 94° C. for 30 seconds, 51° C. for 30 seconds, and 72° C. for 2 minutes followed by 10 minutes at 72° C. A 4° C. hold was used as needed at the end of the cycle.

Figure 7:
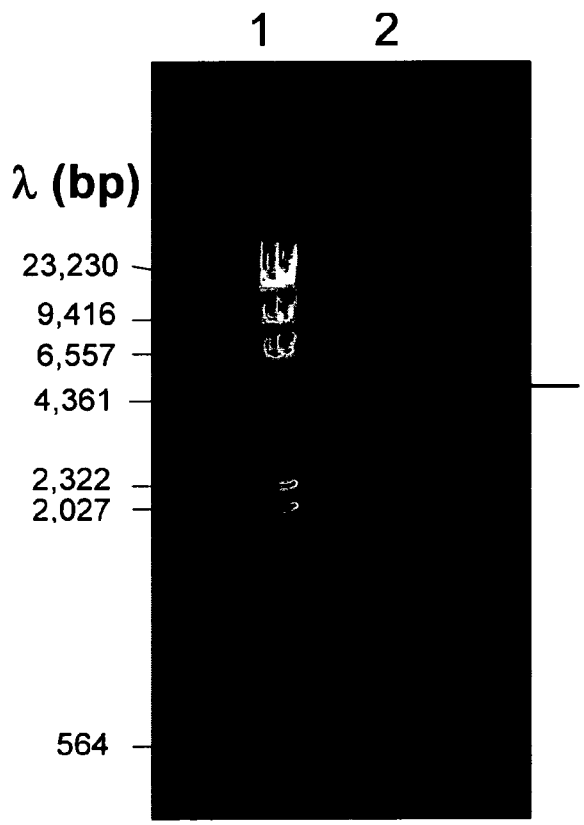
FIG. 7 shows the purified 4.9 Kb PCR product (lane 2) from *P. aeruginosa* containing the bioBFHCD cassette. Lambda HindIII markers are in lane 1.
Figure 8A:
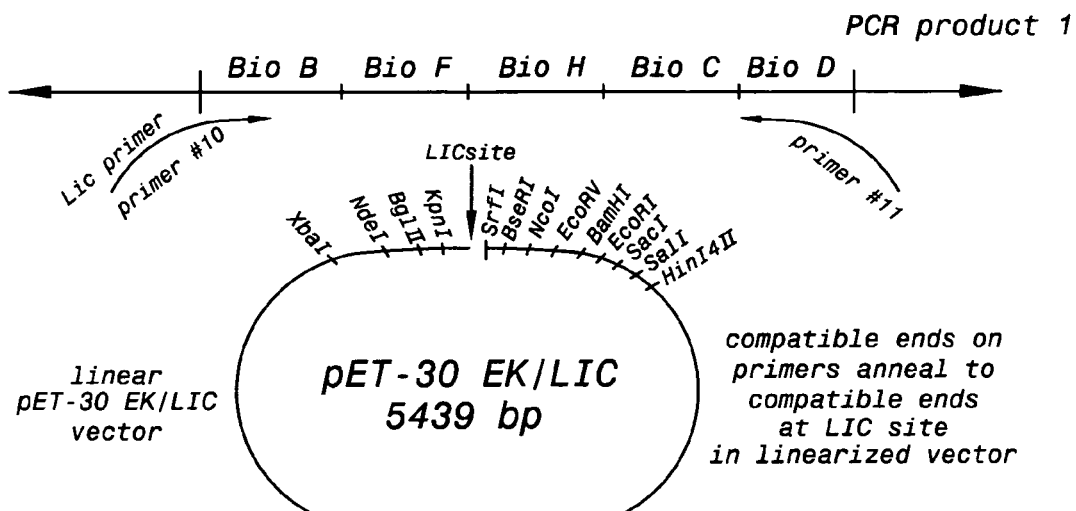
FIG. 8A shows the linearized vector/plasmid cleaved at the LIC site.
Figure 8B:
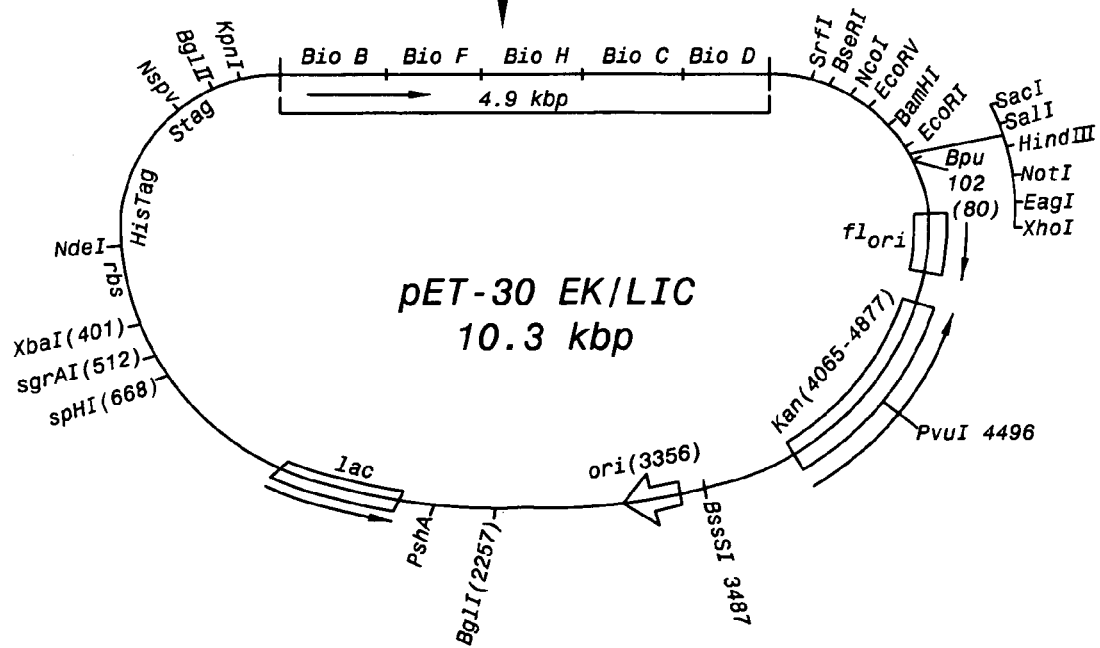
FIG. 8B shows the bioBF-HCD cassette inserted into the pET-30 EK/LIC plasmid.
Figure 9:
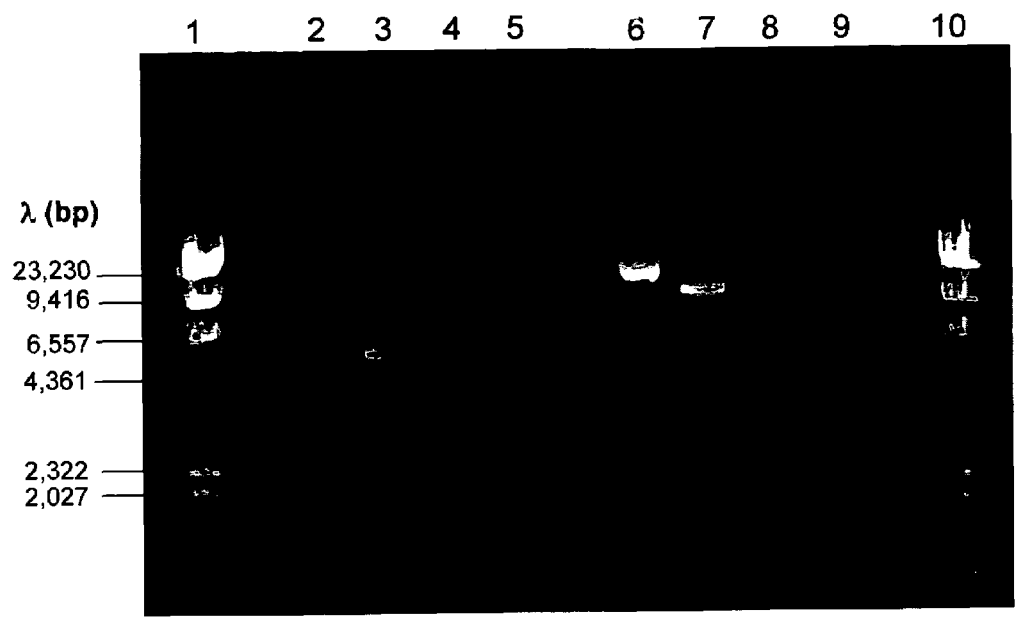
FIG. 9 is a comparison of colonies 14 and 15 screened for proper ligation of the bioBFHCD biotin cassette into the pET-30/LIC plasmid. λHindIII markers are shown in lanes 1 and 10. Colony 14 DNA is shown in lanes 2 through 5. Colony 14 DNA was undigested (lane 2), or digested with XbaI (lane 3), EcoRI (lane 4), or double-digested with XbaI and EcoRI (lane 5). Colony 15 DNA is shown in lanes 6 through 9. Similarly, Colony 15 DNA was undigested (lane 6), or digested with XbaI (lane 7), EcoRI (lane 8), or double-digested with XbaI and EcoRI (lane 9). The 4.9 Kb bioBFHCD cassette for Colony 15 (lane 9) indicates proper insertion of the cassette into the plasmid.

All the reactions were analyzed by agarose gel electrophoresis using standard protocols as described in Sambrook and Russell (2001). Referring now to FIG. 7, the PCR reaction was loaded on a preparative gel for large scale isolation of PCR products. Lambda DNA digested with HindIII restriction endonuclease standards (Invitrogen, Corp.) was used as DNA size standards. The reaction using the colony picked showed a band of interest at 4.9 Kb. The 4.9 Kb band was isolated using Qiagen Gel Extraction Kit (Qiagen, Inc., 27220 Turnberry Lane, Suite 200, Valencia, Calif. 91355). As shown in FIG. 8, the isolated 4.9 Kb bioBFHCD DNA fragment was annealed into the linearized pET-30/LIC vector (5.4 Kb) using kit protocols (EMD Biosciences, Inc./Novagen, Inc., P.O. Box 12087, La Jolla, Calif. 92039-2087). One of ordinary skill in the art would recognize that other vectors could be used without deviating significantly from the principles of the present invention. The 10.3 Kb pET-30/EK/LIC-bioBFHCD plasmid was then transformed into One-Shot™ E. coli (Invitrogen, Corp.) resulting in 96 colonies. From these colonies, 64 were picked, grown and the plasmid DNA was isolated. The plasmid DNA from each colony was digested with EcoRI to verify the size of the insert. Nineteen colonies containing the correct insert were selected and subsequently digested each with EcoRI and XbaI restriction endonucleases (Promega, Corp.), and double-digested with both EcoRI and XbaI to verify proper insert dropout. FIG. 9 shows the expected insert dropout for colonies 14 and 15. The plasmid DNA was purified using a Qiagen Quickprep Spin Column kit. Digests were run on a 1% agarose gel. As shown in FIG. 9, 5.4 Kb and 4.9 Kb bands (lane 9) were observed that correspond to the expected size of the vector (5.4 Kb) and to the bioBFHCD cassette insert (4.87 Kb). Colony 15 displayed optimal banding and was chosen for further study.

Testing of Primary Cassette for Protein Products.

Figure 10:
FIG. 10 shows DNA integrity of Colony 15 expression vector/cassette DNA transformed into competent One Shot™ *E. coli* in, as examples, three of the five selected colonies. All colonies exhibited DNA banding identical to the original DNA of Colony 15. HindIII markers are shown in lanes 1 and 11. DNA was undigested (lanes 2, 5 and 8), digested with XbaI (lanes 3, 6 and 9), or double-digested with XbaI and EcoRI (lanes 4, 7 & 10). All three showed to have the correct insert at 4.9 Kb. All colony DNA exhibited banding identical to the original DNA of Colony 15.

Colony 15 expression vector/cassette DNA was transformed into competent One Shot™ E. coli (Invitrogen, Corp.) and plated as described previously. Five colonies were selected and plasmid DNA isolated. The DNA from each of the five colonies was digested with EcoRI or XbaI, or double-digested with both to test for DNA integrity. All colony DNA exhibited banding identical to the original DNA of colony 15 as shown in FIG. 10 for colonies one through three. DNAs for each of the five colonies were transformed into BLR(DE3) Rec A$^-$ E. coli (Invitrogen, Corp.). Cultures were grown, induced and run on a 12% SDS PAGE gel to test for the presence of proteins that would correspond to the sizes of enzymes in the biotin pathway. All five colonies expressed proteins that properly corresponded to biotin biosynthetic enzymes (data not shown). DNA from the five colonies were purified from the verified colonies grown previously. The isolated DNA was sequenced to verify that the constructs contained correct sequences. This sequence was then BLAST searched using the publicly available software from the National Center for Biotechnology Information at http://www.ncbi.nlm.nih.gov/ to identify similar sequences. This sequence is unique. The third of the five DNAs was chosen for further study. This DNA was given the designation of "3of15."

Addition of the bioA Gene in Reverse Orientation to the Primary Cassette

Figure 11A:
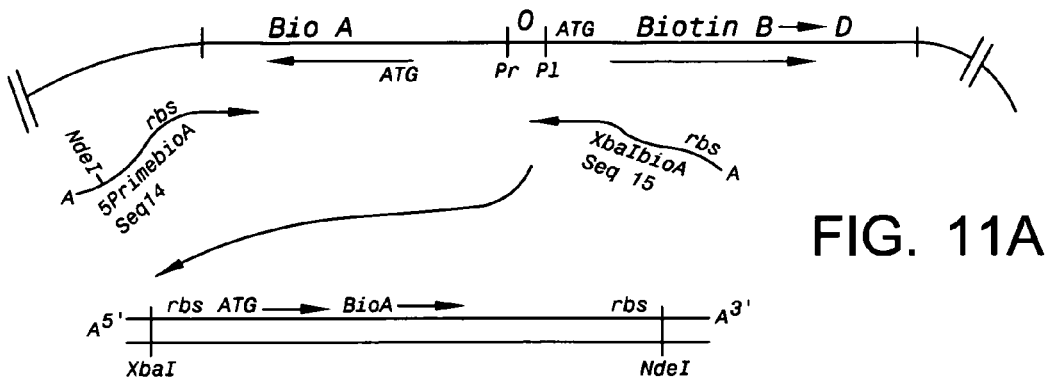
FIG. 11A shows the bioA sequence in its normal chromosomal orientation and the final orientation after amplification by PCR and for insertion into the pCRII-TOPO plasmid which is shown in FIG. 11B.
Figure 11B:
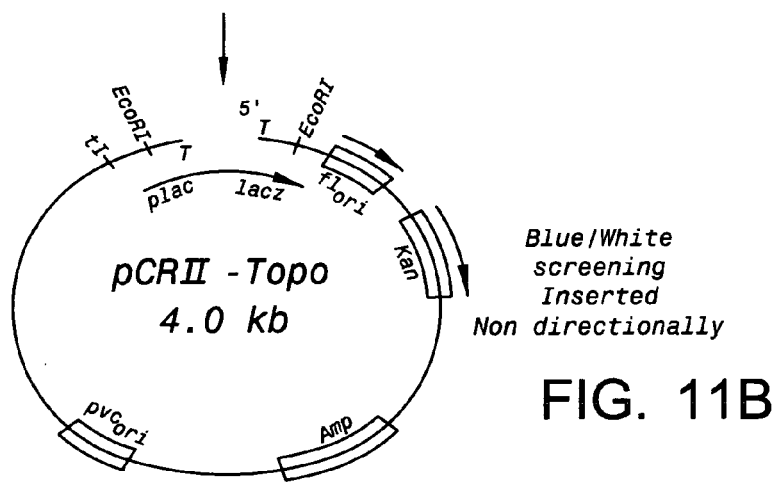
FIG. 11 shows plasmid structures with restriction sites and further showing the insertion of the bioA sequence (1.5 Kb) into the pCRII-TOPO plasmid (4 Kb) to form the pCRII-TOPO-BioA plasmid (5.5 Kb).
FIG. 11C shows the final pCRII-TOPO-bioA plasmid.

BioA in P. aeruginosa is adjacent to the 5-prime end of bioB but in opposite orientation as shown in FIG. 11A. Additionally, the bioA gene has a separate promoter ($P_L$) within the same operator region to that of the bio operon ($P_r$) naturally found in P. aeruginosa (Accession No. NC_002516) but which drives the expression of the gene running in the opposite direction. In the present invention, the bioA gene was inverted and juxtaposed upstream from bioB, as shown in FIG. 6, FIG. 11A, FIG. 11C, and FIG. 12, to permit all of the genes in the complete cassette (bioABFHCD) to be driven by the same or perhaps multiple promoters, thus creating a synthetic biotin operon.

The bioA insert was produced via PCR reaction using P. aeruginosa DNA as a template, set forth in SEQ ID NO: 13, using the same protocol as described above in amplifying the bioBFHCD cassette with the exception that gene specific primers shown in SEQ ID NO: 14 and SEQ ID NO: 15 for bioA were used consisting of novel ribosomal binding sites inserted 5-prime to the bioA gene (shown in FIG. 11A) as well as to bioB using primers shown in SEQ ID NO: 11 (shown in FIG. 8A) and SEQ ID NO: 14. The PCR cycle was similar as described before for other reactions with the exception that the annealing temperature for the primers shown in SEQ ID NO: 14 and SEQ ID NO: 15 with the P. aeruginosa bioA template was 65° C. The PCR reaction produced a unique band of 1.5 Kb, shown in FIG. 14, that corresponds to the bioA gene.

Figure 11C:
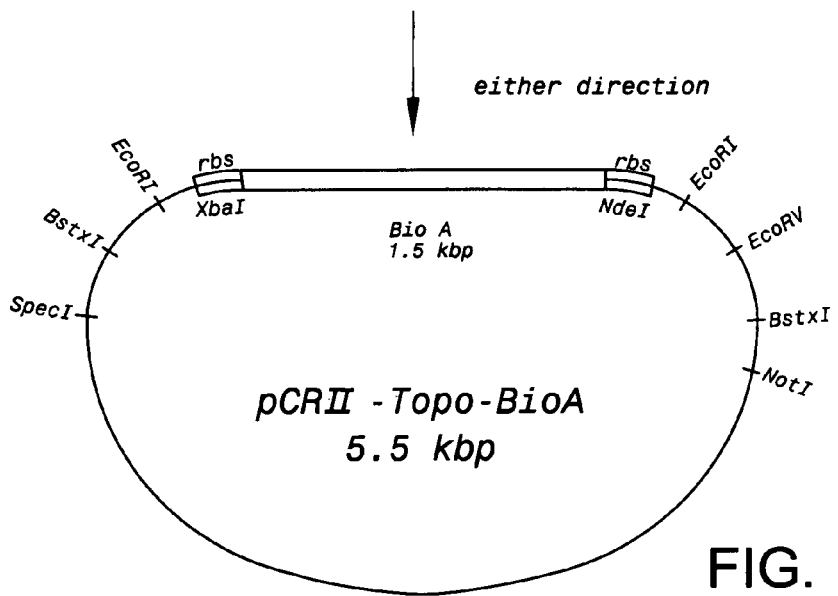
Figure 12A:
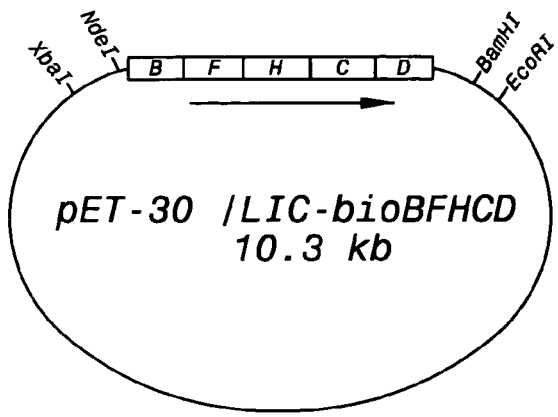
FIG. 12A shows the pET-30 EK/LIC-bioBFHCD plasmid (10.3 Kb).
Figure 12B:
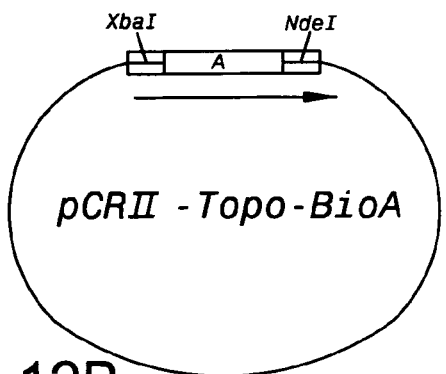
FIG. 12B shows the pCRII-TOPO-bioA plasmid (1.5 Kb).
Figure 12C:
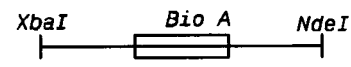
FIG. 12C shows the final pET-30/LIC-bioABFHCD plasmid (approximately 11.7 Kb).
Figure 12D:
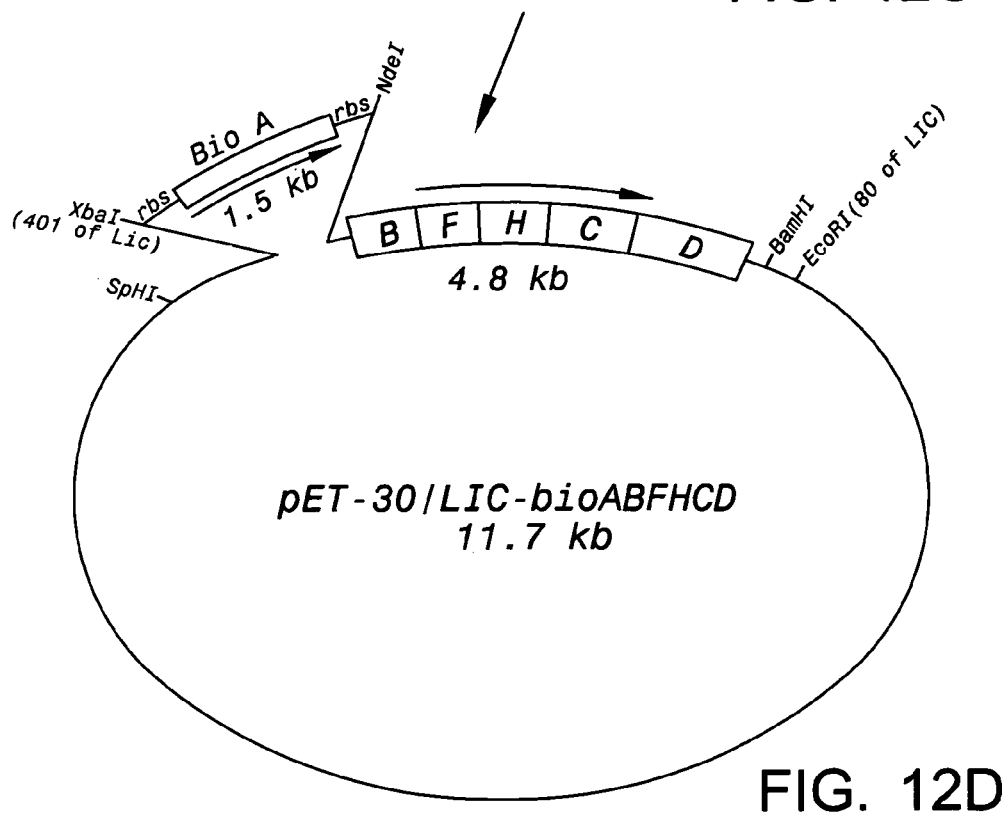
FIG. 12 shows plasmid structures that show the insertion of the bioA sequence (1.5 Kb) in the same orientation and upstream of the bioBFHCD cassette annealed in the pET-30/LIC vector to form the pET-30/LIC-bioABFHCD plasmid.
Figure 13:
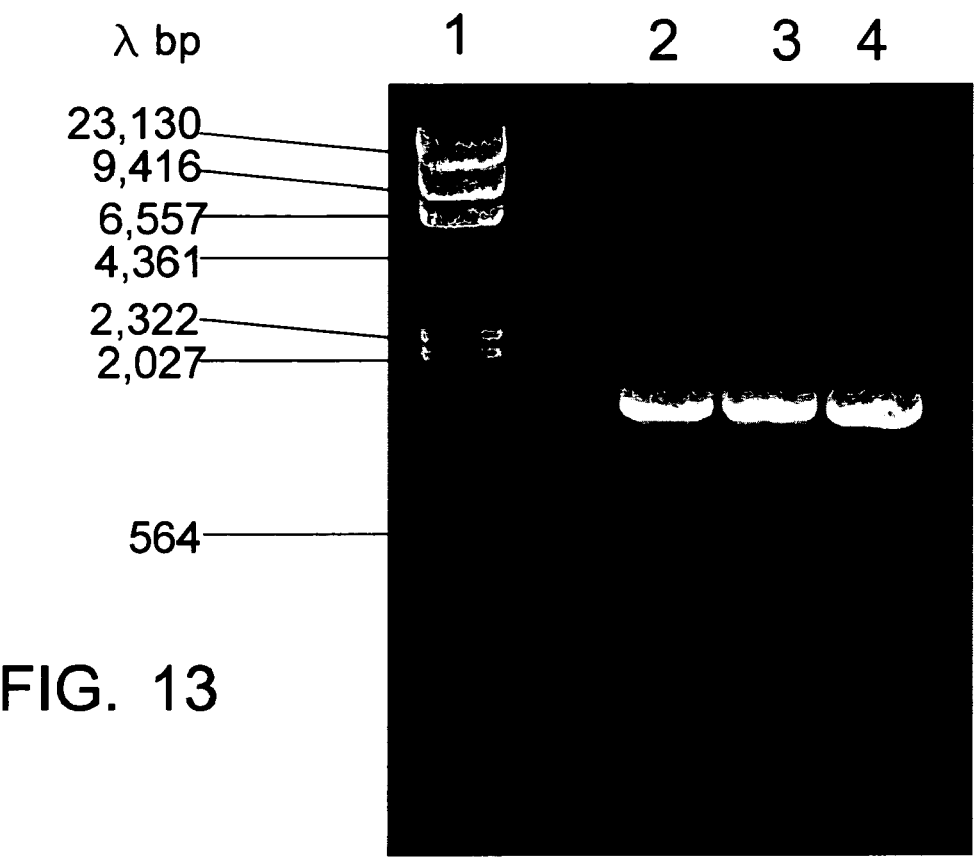
FIG. 13 shows the PCR product of bioA. DNA shown was excised and purified for ligation into the pET-30/LIC-bioBF-HCD vector. Shown are λHindIII markers (lane 1) and the same bioA PCR product in multiple lanes (lanes 2, 3 and 4).
Figure 14:
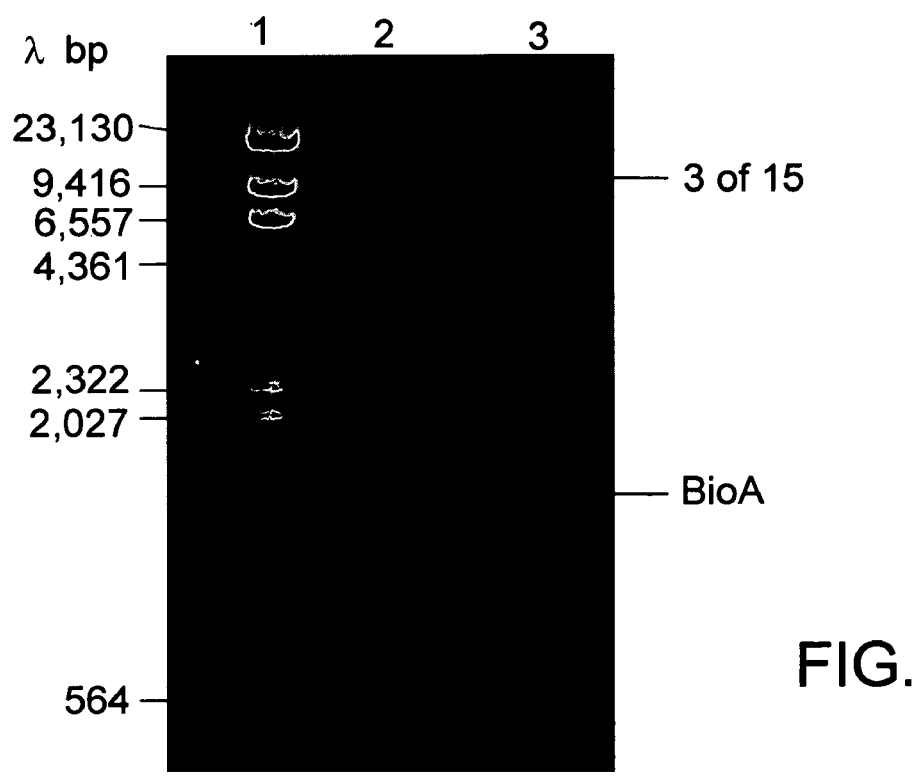
FIG. 14 is a photograph of gel-purified XbaI /NdeI bioA DNA (Lane 2) and 3of15 DNA (Lane 3). Lane 1: λHindIII markers.

After purification, the 1.5 Kb product was inserted into the pCRII-TOPO vector (Invitrogen, Corp.) according to the protocol provided except 1.0 µL of T4 ligase was added. The pCRII/TOPO/bioA vector, shown in FIG. 11C and FIG. 12B is 5.5 Kb. The ligation mix was transformed into competent E.coli One Shot™ cells as before but using 4 µL of ligation mix. E. coli cells carrying this Pseudomonas-derived bioA were plated onto LB agar plates containing either 50 µg/mL Kan or 50 µg/mL Ampicillin (amp) at 10 µL, 25 µL, and 50 µL. Six colonies from the Amp-selected and six from the Kan-selected colonies were picked and grown overnight at 37° C. in LB plus appropriate antibiotic at 50 µg/mL. The plasmid DNA from each of the picked E. coli colonies was purified using Qiagen Quick Spin protocols as before. NdeI, XbaI and double digests were run to test for the presence of the 1.5 Kb bioA dropout. DNAs from colonies 4 and 5 from the amp selection and colonies 1, 2 and 3 from the Kan selection showed the expected dropout at 1.5 Kb as shown in FIG. 14 for colony 3, termed "3of15." Preparative digests were run on these selected colonies as follows to produce enough of the bioA gene to insert into the promoter plasmid containing the remaining biotin cassette, as shown in FIG. 12. FIGS. 12A-12D show the insertion of the bioA sequence (FIG. 12C), excised from the pCRII/TOPO-bioA plasmid (FIG. 12B), in the same orientation and upstream of the 4.9 Kb bioBFHCD cassette producing the bioABFHCD sequence set forth in SEQ ID NO: 16 annealed in the 10.3 Kb pET-30/LIC vector (FIG. 12A) to form the 11.7 Kb pET-30/LIC-bioABFHCD plasmid shown in FIG. 12D.

Figure 17:
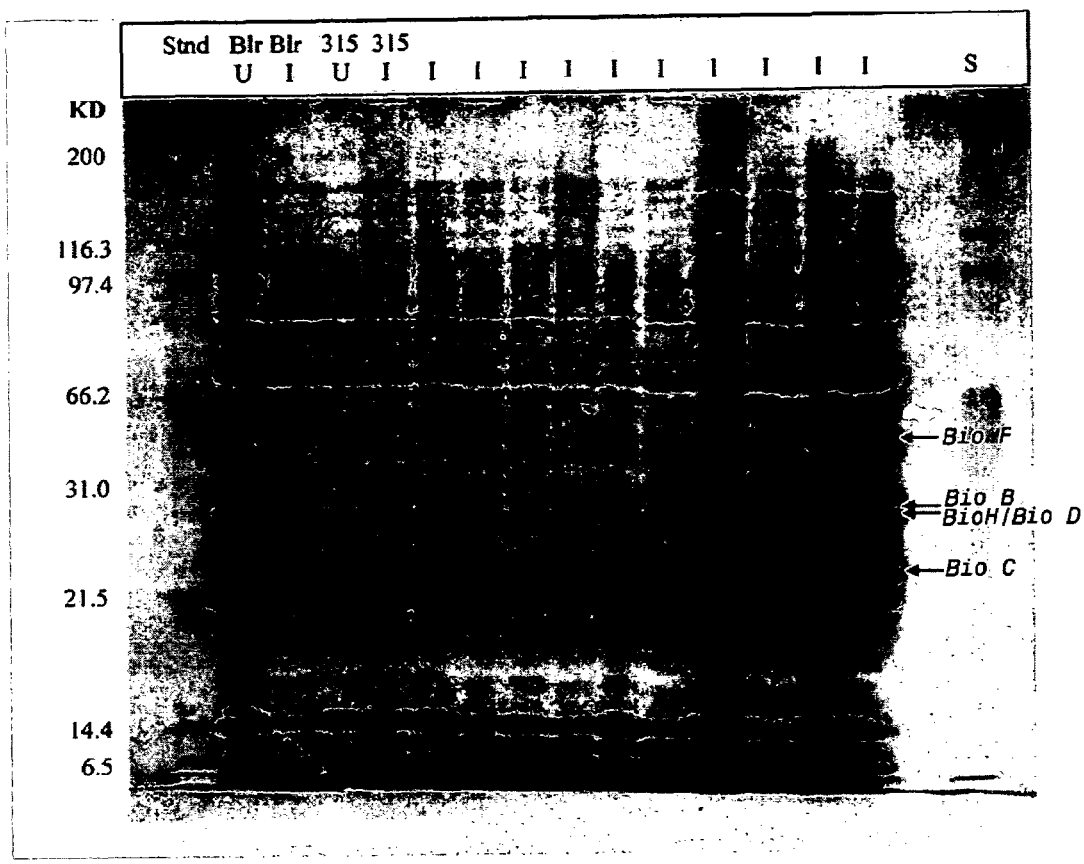
FIG. 17 is a photograph of a 15% SDS-PAGE gel showing correct biotin biosynthetic enzyme gene product banding corresponding to the sizes expected of biotin pathway enzymes in competent BLR cells transformed with 3of15 DNA (labeled "315"). Four colonies were grown and induced with IPTG. "U"=Uninduced and "I"=Induced. Controls were untransformed BLR cells (lacking 3K52 DNA).

The 3of15 DNA was transformed into competent and inducible BLR cells for expression. Four colonies were grown and induced with IPTG as commonly known to one of ordinary skill in the art. See, e.g., Sambrook and Russell, 2001. Cells were prepared and run on 15% SDS-PAGE gels. Controls were BLR cells without 3of15 DNA. The cell lysate was run as induced and uninduced as before with IPTG. As shown in FIG. 17, these gels showed protein-banding corresponding to the sizes expected for the BFHCD enzymes based upon the P. aeruginosa sequence (Accession No. NC_002516) indicating these E. coli cells produced the P. aeruginosa biotin biosynthesis enzymes. The molecular weight for each enzyme was predicted and are provided in Table 1.

TABLE 1

Molecular masses of gene products from BIO operon

| Protein | Size (MW) |
|---------|-----------|
| Bio A   | 52,477    |
| Bio B   | 39,000    |
| Bio F   | 41,000    |
| Bio H   | 28,500    |
| Bio C   | 25,000    |
| Bio D   | 28,000    |

Figure 15:
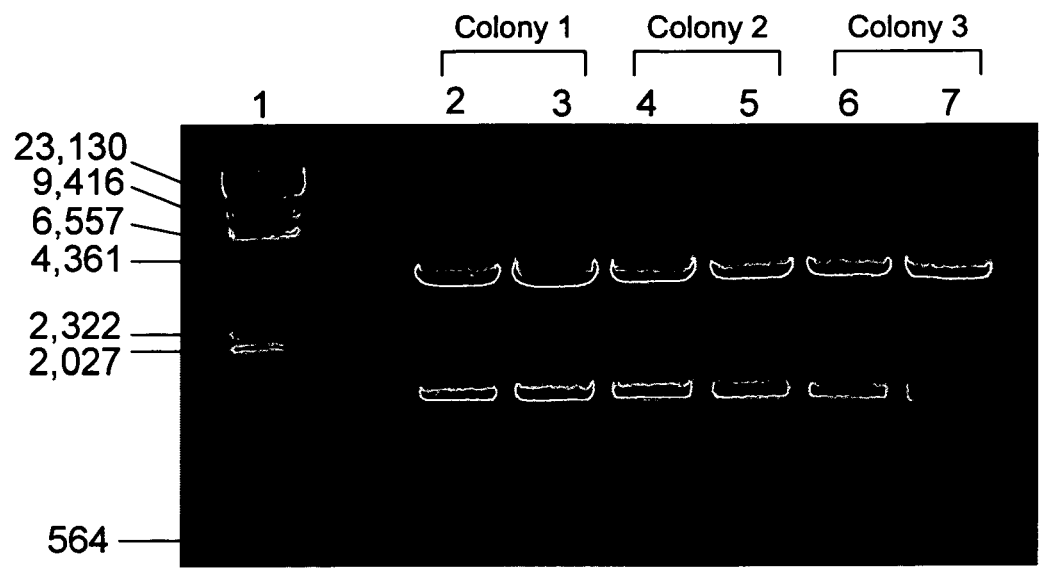
FIG. 15 is a photograph showing correct insertion of gel-purified bioA into the pCRII-TOPO vector in three colonies. λHindIII markers are shown in Lane 1. Colony 1 is shown in Lanes 2 and 3. Colony 2 is shown in Lanes 4 and 5. Colony 3 is shown in lanes 6 and 7. DNA was digested with XbaI/NdeI to verify the 1.5 Kb dropout corresponding to the bioA insert.

Insertion of the bioABFHCD Cassette into the p519gfp Promoter Foundation Plasmid The DNAs from three colonies 1, 2 and 3 from the Kan selection for the bioA insert were each separately ligated into the previously XbaI/NdeI-digested 3of15 DNA using T4 DNA ligase (Promega, Corp.). Proper ligation was verified and is shown in FIG. 15.

Figure 16:
FIG. 16 is a photograph of a DNA gel confirming ligation of the bioABFHCD cassette into the pET-30/LIC vector. λHindIII DNA markers are shown in lanes 1 and 14. Colony 50 DNA was undigested (lane 2) or digested with XbaI (lane 3), NdeI, (lane 4), or double digested with XbaI and NdeI (lane 5). Colony 51 DNA was also undigested (lane 6), digested with XbaI (lane 7) or NdeI (lane 8) or double-digested with XbaI and NdeI (lane 9). Similarly, Colony 52 DNA was undigested (lane 10), digested with XbaI (lane 11) or NdeI (lane 13) or double-digested with XbaI and NdeI (lane 13). Colony 52 shows the expected banding.

Each ligation was transformed into One Shot™ competent cells and plated. Several ligations and transformations were completed to generate enough colonies to go forward with screening. Each colony was picked and grown overnight in LB containing 50 μg/mL Kan. Colonies were designated 3K1 through 3K60, 4K1 through 4K29, and 5K1 through 5K24. The plasmid DNA was purified as before using Qiagen Quickspin kit protocol. In each case, digests of the colony plasmid DNAs were run using XbaI, NdeI, and XbaI /NdeI as described above for bioA. As shown in FIG. 16 (lane 13), colony 3K52 showed the proper banding and it was chosen for further study.

Addition of Complete Biotin Cassette to Host Used for Biotin Production

Figure 18:
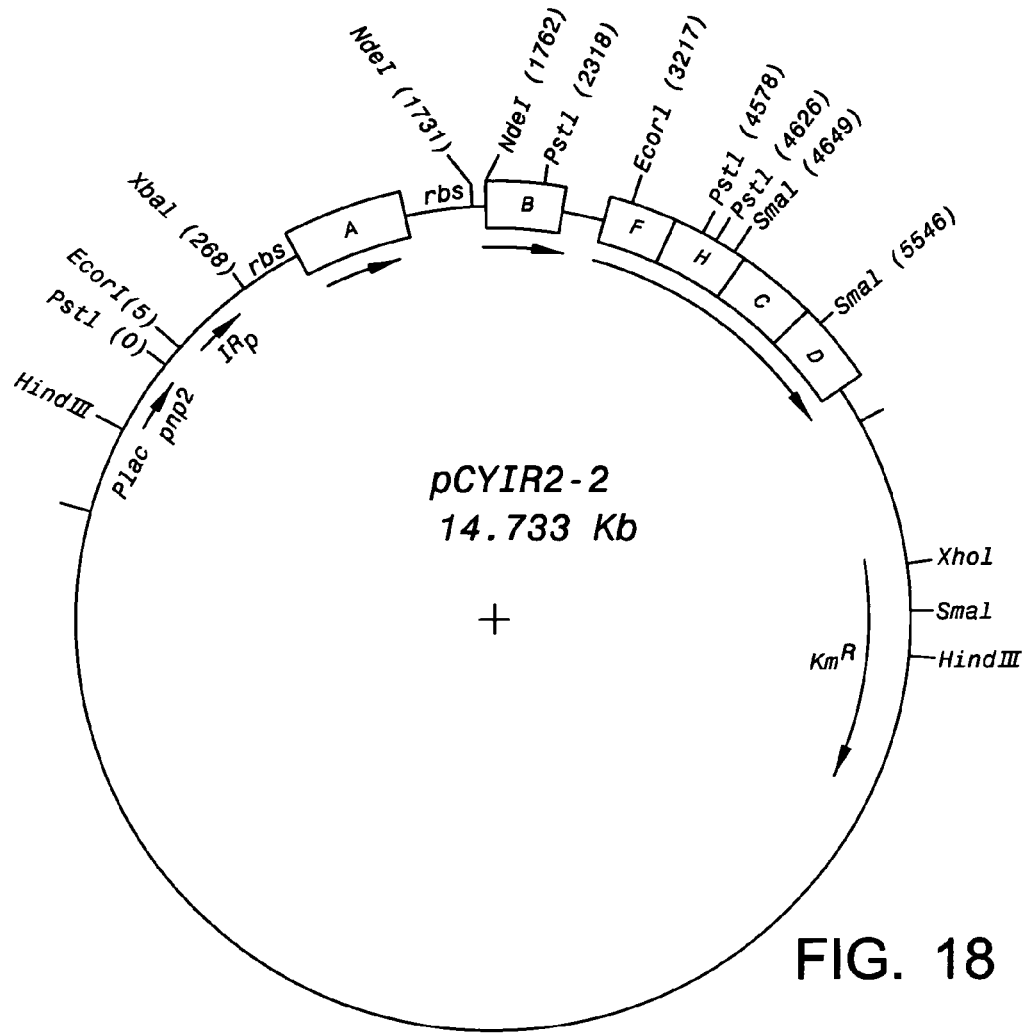
FIG. 18 shows the final construct termed pCYIR2-2 with the bioABFHCD cassette driven by the Pf1 IR promoter and used according to one embodiment of the invention.
Figure 19:
FIG. 19 is a photograph of a gel of digested IR2-2 DNA showing bands corresponding to 4.6 Kb and about 3.3 Kb. Lanes 1 & 5 are λHindIII standards. IR2-2 DNA is undigested (lane 2), digested with EcoRI (lane 3), or digested with BamHI (lane 4). Lane 2 is EcoRI digest producing 3 visible bands: Largest=~4.6 Kb, two visible bands very close together representing really 3 based on intensity of bands=top is 2×~3430 with lower being 1×~3203. Lane 4 is BamHI digest which linearizes the plasmid to provide a single band size of 14.7 Kb.

DNA from 3K52 was transformed into *E. coli* and each of the p519-promoter plasmids for each of the Pf1 IR, G8 and consensus promoter DNAs was transformed into the *P. mutabilis* mutant host (1F9). Cells were plated onto LB agar/Kan plates for selection. The plates were incubated at 37° C. overnight. Colonies were picked, grown overnight, and plasmid DNA was purified as before. The promoter plasmids G8, IR, and consensus sequence were digested with EcoRI while the 3K52 DNA was digested with BamHI restriction endonuclease. Each of the recesses formed were filled in with Klenow fragment (Promega, Corp.) for subsequent blunt end ligation of the two incompatible ends. The reaction was allowed to proceed for 10 minutes at room temperature then incubated at 75° C. for 10 minutes to heat inactivate the Klenow fragment. At room temperature 5 μL of XbaI was then added to each of the blunt end fragments. The digestion reaction was allowed to react overnight at 37° C. These reactions were gel purified as before. The 3K52 DNA was ligated with each of the prepared promoter DNAs to form three separate DNAs that each consisted of a unique promoter and the complete biotin cassette. Each ligation mixture was incubated at room temperature for 4 hours. The final construct is shown in FIG. 18. The ligation mix was then transformed into competent 1F9 *P. mutabilis* cells. FIG. 19 shows that 1F9 mutant cells produced DNA fragments corresponding to the correct sizes predicted for IR2-2 DNA digested with EcoRI and BamHI. The recovered cells were plated onto LB agar/Kan.

Figure 20:
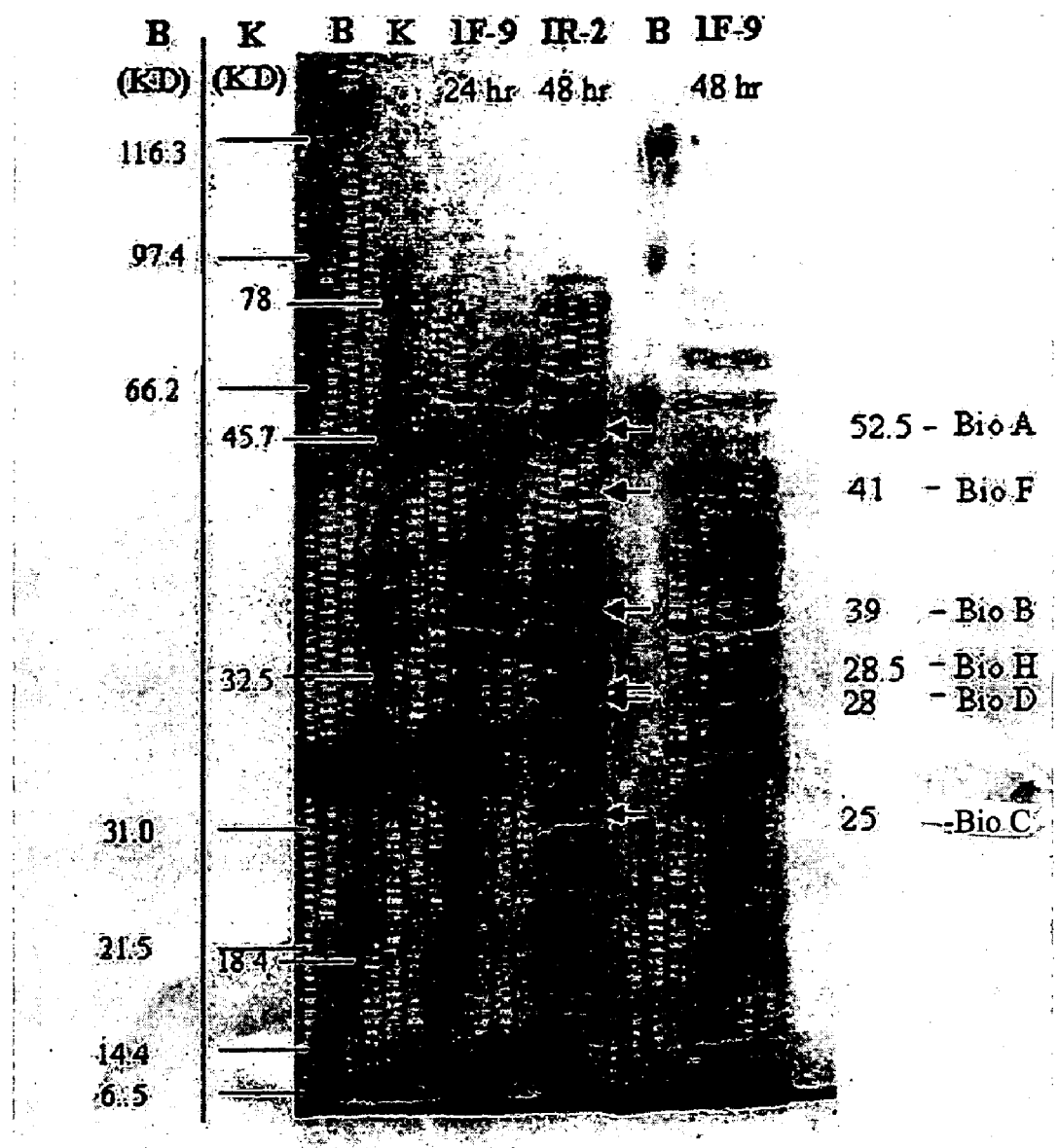
FIG. 20 is a photograph of a 12% SDS-PAGE gel showing production of recombinant biotin synthesis enzymes coded by the IR2-2 cassette (see FIG. 6) expressed in the 1F9 *P. mutabilis* mutants. B=broad range SDS standards; K=Kaleidoscope protein standards; 1F9=host only; IR2=1F9 transformed with the IR2-2 plasmid (see FIG. 18). Arrows point to proteins corresponding to recombinant biotin biosynthetic enzymes encoded by the biotin IR2-2 cassette.

FIG. 20 shows that transformed *P. mutabilis* 1F9 host cells produce proteins that correspond to the molecular weights of biotin operon gene products. FIG. 20 is a photograph of a 12% SDS-PAGE gel showing production of recombinant biotin synthesis enzymes coded by the IR2-2 cassette expressed in the 1F9 *P. mutabilis* mutants. Mutated *P. mutabilis* cells were grown for 24 hours and 48 hours in production medium. Cells (10 mL) were centrifuged at 6,000 ×g for 30 minutes, resuspended in 1 mL of lysis buffer (50 mM Tris, pH 8.0, 100 μg PMSF), followed by 3 freeze-thaw cycles and sonicated in five bursts of 30 seconds. Fifty micrograms of total protein was loaded onto a 12% SDS PAGE gel (see FIG. 20). Protein bands representing BFHCD and A were evident as overexpressed on the gel (indicated by arrows).

Verification and Selection of Complete Cassette.

Six colonies from each promoter type were grown in LB media overnight. The cells were centrifuged and the supernatant was evaluated for biotin production using HABA reagent (Sigma-Aldrich). The IR promoter cells exhibited the greatest change in absorbance. The DNA designated IR2-2 was chosen to use directly for optimization of production of biotin. FIG. 19 shows the plasmid map of the IR2-2 DNA used for the current production of biotin.

Deposit Statement

The subject cultures listed below are deposited under conditions that assure that access to the cultures will be available during the pendency of the patent application disclosing them to one determined by the Commissioner of Patents and Trademarks to be entitled thereto under 37 C.F.R. 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit, or the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The culture for mutant *P. mutabilis* transformed with the bioABFHCD construct (1F9/pCYIR2-2) has been deposited at the American Type Culture Collection (ATCC) located at 10801 University Blvd., Manassas, Va. 20110-2209, U.S.A. and assigned number PTA-6904.

Production of Biotin in 1F9 *P. mutabilis*

Quantification of Biotin and Dethiobiotin In Vitro Synthesis of Biotin

The activity of the recombinant enzymes was tested by performing an in vitro assay of total biotin produced from enzymes in the cell lysate of the 1F9 *P. mutabilis* mutant harboring the p519 biotin bioABFHCD cassette, pCYIR2-2, shown in FIG. 18. Enzyme activity was assayed using a method developed based on pathway information provided by Marquet et al, 2001. See also Birch et al., 1995 and Ifuku et al., 1994. Biotin synthase (BioB) converts dethiobiotin (DTB) to biotin. The biotin synthase enzyme is coupled to a flavodoxin reductase enzyme which converts NADPH to NADP. Oxidation of NADPH is consistent with a decrease in light absorbance at 340 nm and reflects biotin synthase activity and biotin production.

A reaction mix was prepared consisting of 50 mM TRIS, pH 8.0, 2 mM DTT, 0.5 mM Fe.gluconate, 0.6 mM NADPH, 0.25 mM S-adenosylmethione, 5 mM fructose 1,6-bis phosphate, 0.5 mM L-cysteine, 0.5 mM alanine and 1 mM thiamine pyrophosphate and 0.5 mM pimelic acid. The absorbance at 340 nm was monitored detecting the conversion of NADPH to NADP+ by biotin synthase. The intention was that if the p519-CYIR2-2 biotin cassette was expressing all of the biosynthetic enzymes, the conversion of the basic precursors L-alanine, L-cysteine, and pimelic acid to biotin would be observed. The biotin specific enzymes were targeted by varying the amounts of pimelic acid and S-adenosyl methionine (SAMe) due to both of these components being essential for biotin synthesis. Pimelic acid is crucial for the gene products of bioC and bioH to convert pimelate to pimeloyl CoA. SAMe is a methyl carrier essential for biotin production at two key steps: (1) conversion of 8-amino-7-oxopelargonate to 7,8-Diaminopelargonate by DAPA synthase (Ploux et al. 1999, Webster et al. 2000, Marquet et al., 2001) and (2) as a cofactor of biotin synthase enzyme in the conversion of dethiobiotin to biotin.

Figure 21:
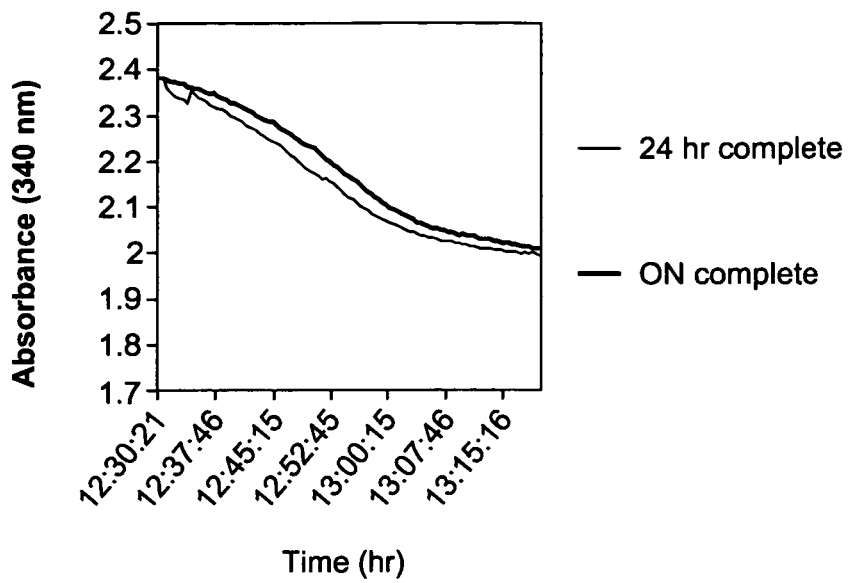
FIG. 21 is a spectrophotograph demonstrating diminished absorbance corresponding to the oxidation of NADPH to NADP that reflects biotin synthase (BioB) activity and biotin production in cell free lysates of mutant 1F9 *Pseudomonas mutabilis* expressing the bioABFHCD cassette of the IR2-2 plasmid.

FIG. 21 is a spectrophotograph that demonstrates biotin production via the DACA assay by mutant *P. mutabilis* transformed with the pCYIR2-2 plasmid. Cells were grown for 24 hours, harvested by centrifugation at 4° C. at 6000×g for 30 minutes. The cell pellet was lysed by freeze-thawing three times followed by sonication in 30 second pulses. The cell debris was removed by centrifugation at 14000×g for 10 minutes at 4° C. The total protein of the supernatant was determined using the assay of Bradford (1976). Bradford reagent was obtained from BioRad (Hercules, Calif.) 100 g of total protein was used per reaction. In a 96-well microtiter plate, substrate mix was added consisting of 50 mM Tris pH 8.0, 5 mM MgCl2, 2 mM DTT, 0.5 mM FeCl2, 0.6 mM NADPH, 0.25 mM SAM, 0.5 mM L-Cys, 0.1 mM Thiamine, 0.5 mM L-Ala, and 0.5 mM Pimelic acid.

Figure 22:
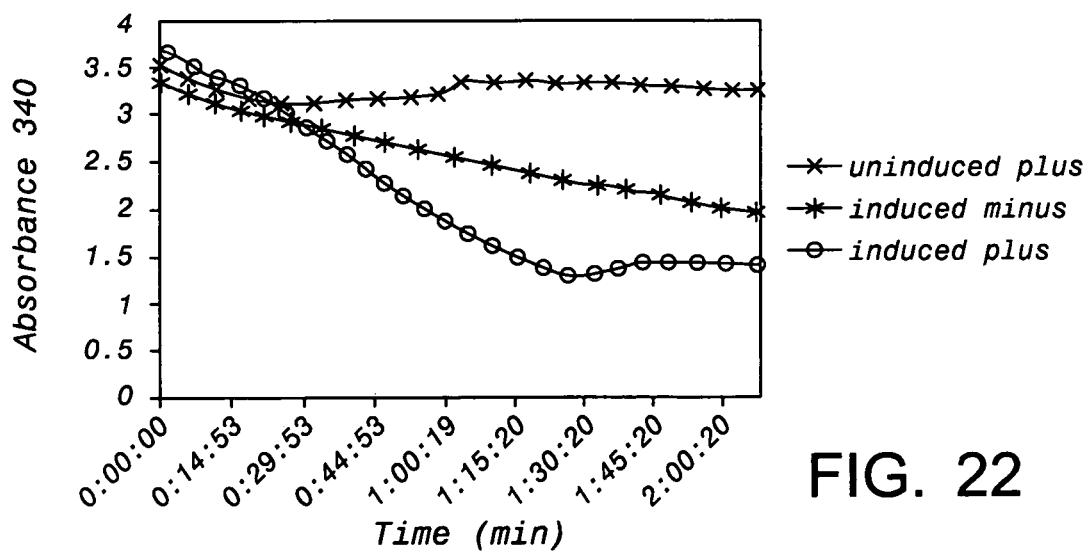
FIG. 22 shows in vitro biotin biosynthetic enzyme activity by *E. coli* host cells expressing the bioBFHCD DNA cassette in pET30-LIC. Conversion of NADPH to NAD+ by enzymes expressed upon induction of 3of15 plasmid in the BL21 (DE3) *E. coli* cells. Enzymes expressed from coding regions of the bioBFHCD cassette inserted in the pET30-LIC plasmid. Induced with IPTG to initiate synthesis from the Lac promoter. "Uninduced"=cell extract from cells not induced with IPTG. "Induced"=IPTG-induced cell extract containing reaction mix (without SAMe) was added. "Induced plus" consisted of IPTG induced extract plus SAMe added to the reaction mix.

In addition, FIG. 22, shows expression of the bioBFHCD cassette in the 3of15 plasmid in *E. coli* induced with IPTG. Synthesis of biotin from incubation of the lysate with the above reaction mix was 1.8 µmoles/hr/mg biotin synthase based on the biotin synthase enzyme representing 2% of the total protein. Purification of the biotin cassette gene products, such as enzymes, may be done through a combination of ammonium sulfate precipitation and anion exchange chromatography as well as other techniques known to one of ordinary skill in the art. Enzymes may be used in batch to synthesize biotin in vitro as well as each of the enzymes can be linked, for example, to a sepharose stationary column through crosslinking to CnBr activated Sepharose (Amersham-Pharmacia, Corp.) to provide an enzyme-linked synthesis for each intermediate compound. One of ordinary skill will appreciate that the enzymes may be used individually to enhance or produce intermediate precursors for biotin. Therefore, any one or all of the following compounds can be made with the expressed compounds according to the teachings of the present invention: 8-Amino-7-oxopelargonic Acid, 7-Keto-8-aminopelargonic acid (KAPA), 7,8-Diaminopelargonic acid (DAPA), Dethiobiotin (DTB), biotin and pimeloyl-CoA.

Total Biotin Production In Vivo

Growth Conditions

Media components necessary for producing biotin were determined by comparing the total biotin produced in 500 mL of varying carbon sources such as glucose, lactose, fructose, sucrose, corn (steep liquor), protein, amino acid (source of sulfur), phosphate, cations, metals, and necessary precursors for all enzymes in the biotin pathway. Temperatures for growth range from ambient room temperature to 37° C. Production has been observed with minimal and maximal aeration with agitation sufficient for mixing. The pH was maintained at about 8.0 by adding either 1 N $H_3PO_4$ acid or 0.5 N KOH/0.5 N NaOH base.

Total biotin was detected using the DACA assay and converted to the total g/L in the fermentor. A microtiter assay for the determination of the total biotin was developed based on the method described by McCormick and Roth (1970) using 4-dimethylaminocinnam-aldehyde ("DACA") (Sigma-Aldrich Corp.) and sulfuric acid. DACA (p-Di-methyl-amino-cinnamaldehyde) specifically binds the N1 nitrogen of the ureido portion of biotin to form a red reaction product with absorption at 533 nm. A 0.2% w/v DACA in 100% ethanol and a 2% v/v $H_2SO_4$ in 100% ethanol stock solutions were prepared fresh. In a 1.5 mL micro-centrifuge tube, sample was added with the total volume of sample being 100 µL (water was used to make up any difference in volume). To this sample, 100 µL of 0.2% DACA was added and mixed by vortexing. One hundred microliters of the 2% sulfuric acid solution was added and the sample vortexed. To this reaction mix, 700 µL of water was added and the reaction was incubated for 30 minutes. The samples were then either transferred to a cuvette and the absorbance measured at 533 nm or 200 µL of sample was transferred to a 96 well microtiter plate and the absorbance read at 533 nm. For each set of samples measured, a standard curve was prepared using biotin (Sigma-Aldrich Corp.) in concentrations ranging from 0-5 mg/mL.

Figure 23:
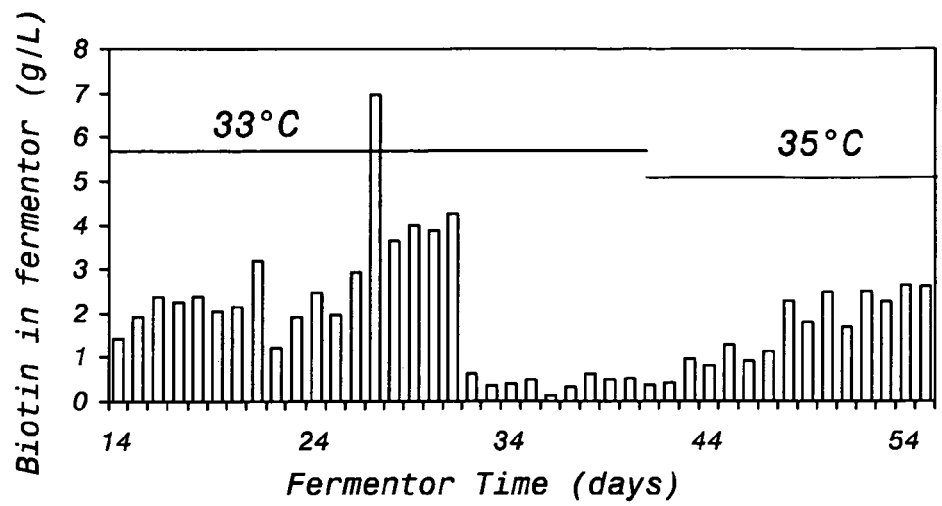
FIG. 23 shows biotin production in excess of six grams per liter assessed by the DACA assay of 1F9 *P. mutabilis* mutants, transformed with the IR2-2 plasmid that encodes the bioABFHCD cassette, grown in continuous culture.

Growth conditions for biotin production were determined. Temperature, agitation and oxygen concentration were varied. Bacteria were grown as previously described and placed in a BioFlo IV, 20 L bioreactor (New Brunswick Scientific) and maintained at pH 8.0. FIG. 23 shows an example analysis of mutant 1F9 *P. mutabilis* (harboring the pCYIR2-2 plasmid) grown in continuous culture using the growth media shown in Example 1 through 56 days shifting temperatures from 33° C. and 35° C. during fermentation. Using the formulation of Example 1, optimal biotin production was at 33° C. with minimal air sparge (approximately 5 PSI) and minimal agitation. Air sparge and agitation were increased from day 32 through 42 resulting in less biotin being produced. Biotin production declined as the temperature increased. The initial conditions (through day 31) were minimal air sparge and agitation so as to prevent cells from settling. Increased air sparge was continued through days 43 to 56 with temperature being the only variable. Days 1 through 13, which are not shown, were grown at 30° C., minimal air sparge and agitation, with no biotin produced suggesting temperatures greater than 30° C. are necessary for biotin production but optimal at 33° C. Other examples include increasing or decreasing the concentrations of the individual components as well as substitutions for yeast extract and tryptone with equivalent fermentative by-products from yeast and other microorganisms.

EXAMPLE 1

| | |
|---|---|
| Tryptone | 20 g |
| Yeast extract | 20 g |
| NaCl | 10 g |
| Na$_2$S | 100 µM |
| FeS$_2$ | 100 µM |
| KCO$_3$ | 50 mM |
| Cysteine | 100 µM |
| Pimelic acid | 100 µM |
| Alanine | 100 µM |
| Na$_2$HPO$_4$ | 25 µM |
| KH$_2$PO$_4$ | 25 µM |
| MgCl | 50 µM |
| 1% whey | |

Media concentrations for 1.0 L

More optimal growth conditions were identified whereby transformed mutant *P. mutabilis* yield biotin at concentrations greater than 15 grams per liter. The more optimal growth conditions are shown in Example 2. The media formulation listed in Example 2 to date has resulted in the 1F9 mutant *P. mutabilis* transformed with the pCYIR2-2 producing as much as 15 g/L of total biotin after about two weeks. Production was carried out in a 10 L B 110 bioreactor (New Brunswick) at 33° C., minimal agitation and air sparge (approximately 5 PSI), with pH controlled at pH 7.8 with automatic acid (1N phosphoric acid) and base (0.5 N sodium hydroxide/0.5 N potassium hydroxide). 7.5 L were grown in a batch environment and at day 14, 4 L of culture was harvested. Cells were centrifuged away and resulting supernatant was assayed directly using the DACA assay as described above. A 1/10 dilution was made of the media into water to eliminate contributions due to media with 10 μL, 25 μL and 100 μL of the 1/10 being assayed along with a standard curve of d-Biotin (Sigma) ranging from 0 μg to 500 μg. Results indicated 15 g/L of total biotin being produced in the fermentor.

EXAMPLE 2

| | |
|---|---|
| Luria-Bertani Broth | 50.0 g |
| 2.0% Whey | 20.0 g |
| L-Cysteine | 0.788 g |
| Pimelic Acid | 1.602 g |
| L-Alanine | 0.445 g |
| $Na_2S$ | 2.40 mg |
| $FeCl_2$ | 1.27 mg |
| $Na_2CO_3$ | 5.30 mg |
| $Na_2HPO_4$ | 3.55 mg |
| $KH_2PO_4$ | 3.40 mg |
| $MgCl_2$ | 20.33 mg |

Media concentrations for 1.0 L

HPLC Analysis of Biotin and Dethiobiotin

Figure 24:
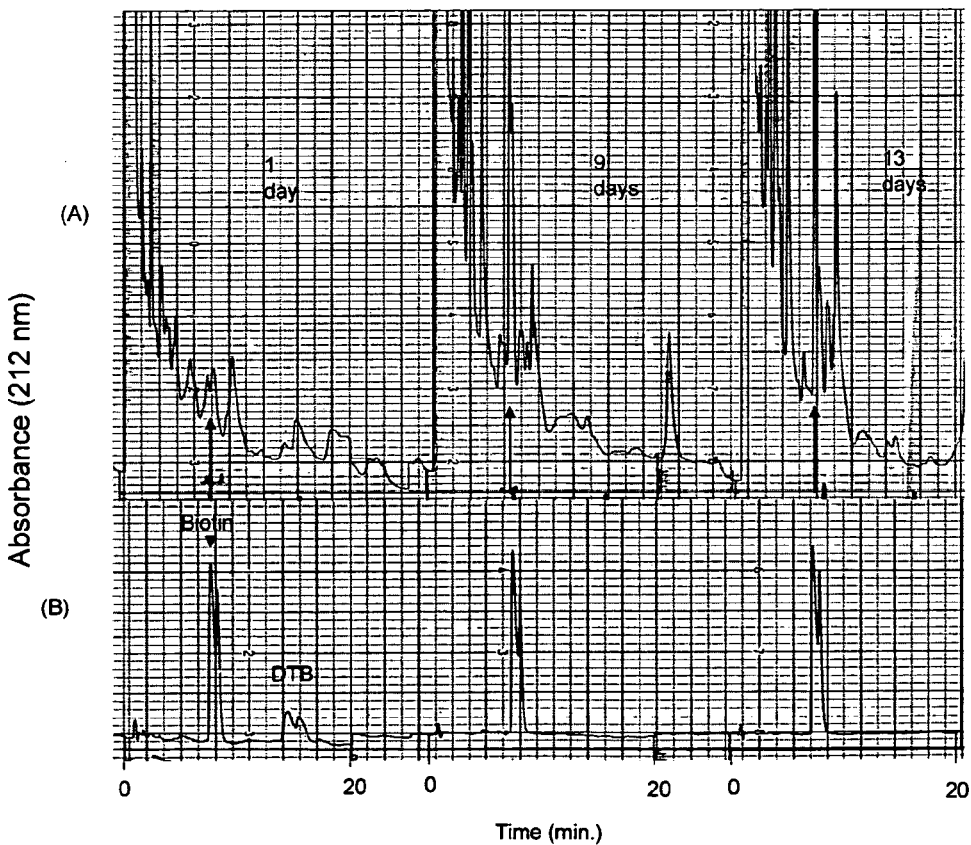
FIG. 24 is a HPLC chromatogram showing the amount of biotin produced by the 1F9 *P. mutabilis* cells transformed with the IR2-2 plasmid containing the bioABFHCD cassette in an embodiment of the present invention. Panel A is a trace of supernatant. Panel B shows standards of biotin and d-dethiobiotin. Panels A and B are the same scale.

HPLC analysis confirmed that the total biotin was greater than 95% biotin. Samples from the fermentor are acidified to pH 2.2. The solution was centrifuged to clarify. The supernatant was decanted to activated charcoal to bind the biotin present. The mixture was mixed well by rocking for 20 minutes. The solution was then centrifuged at 3500 RPM to pellet the charcoal. Ammonium hydroxide (10%) in 52.3% ethanol in water was added to elute the biotin from the charcoal. Samples were immediately acidified to pH 2.5 to prevent degradation of biotin product. This eluant was then analyzed on a ZORBAX extend-C18 reverse phase 4.6×100 mm column packed with 3.5 m resin (Agilent Technologies, Inc., 395 Page Mill Rd., Palo Alto, Calif. 94306). The HPLC conditions consisted of 5% acetonitrile: 95% water acidified to pH 2.2 with concentrated phosphoric acid as described elsewhere (Ekpe A E and Hazen C, 1998). A typical HPLC chromatogram of the charcoal extracted media is shown in FIG. 24. Biotin eluted at 7.5 minutes with the following conditions of 2 mL/min with detector set at 212 nm. Dethiobiotin (DTB) when present eluted at 15 minutes clearly separated from the biotin for easy detection. The amount of biotin was determined based on the area observed under the HPLC peaks of known concentrations of biotin. Under growth conditions described above, all biotin produced was d-biotin, no dethiobiotin was detected.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

REFERENCES

Birch O M, Fuhrmann M, and Shaw N M, "Biotin Synthase from *Esterichia coli*, an Investigation of the Low Molecular Weight and Protein Components Required for Activity in Vitro," The Journal of Biological Chemistry, Vol. 270, No. 32, p. 19158-19165, August 1995.

Bower S, Perkins J B, Yocum R R, Howitt C L, Rahaim P, and Pero J, Cloning, "Sequencing, and Characterization of the *Bacillus subtilis* Biotin Biosynthetic Operon, J. Bacteriol," Journal of Bacteriology, Vol. 178, No. 14, p. 4122-4130, July 1996.

Bradford M M, "A rapid and sensitive method for the quantitation of microgram quantities of protein utilizing the principle of protein-dye binding," Analytical Biochemistry, Vol. 72, p. 248-254, 1976.

Brown S W and Kamogawa, K, "The Production of Biotin by Genetically Modified Micro-organisms," Biotechnology and Genetic Engineering Reviews, Vol. 9, p. 295-326, December 1991.

Ekpe A E and Hazen C, "Liquid chromatographic determination of biotin in multivitamin-multimineral tablets," Journal of Pharmaceutical and Biomedical Analysis, Vol. 16, p. 1311-1315, 1998.

Gibson K et al., "Dethiobiotin Synthetase: The Carbonylation of 7,8-Diaminononanoic Acid Proceeds Regiospecifically via the N7-carbamate," Biochemistry, Vol. 34, p. 10976-10984, 1995.

Green N M, "Spectrophotometric determination of avidin and biotin," Methods in Enzymology," Vol. 18, p. 418, 1970.

Ifuku O, Koga N, Haze S, Kishimoto J, and Wachi Y, "Flavodoxin is required for conversion of dethiobiotin to biotin in *Escherichia coli*," Eur. J. Biochem., Vol. 224, p. 173-178, 1994.

Marquet A, Tse Sum Bui B, Florentin D, "Biosynthesis of Biotin and Lipoic Acid," Vitamins and Hormones, Vol. 61, p. 51-101, 2001.

Matthysse A, Stretton S, Dandie C, McClure N, and Goodman A, "Construction of GFP vectors for use in Gram-negative bacteria other than *Escherichia coli*," FEMS Microbiology Letters, Vol. 145, p. 87-94, 1996.

McCormick D and Roth J A, "Specificity, Stereochemistry, and Mechanism of the Color Reaction between p-Dimethylaminocinnamaldehyde and Biotin Analogs," Analytical Biochemistry, Vol. 34, p. 226-236, 1970.

Otsuka A J, Buoneristiani M R, Howard P K, Flamm J, Johnson C, Yamamoto R, Uchida K, Cook C, Ruppert J, Matsuzaki J, "The *Escherichia coli* Biotin Biosynthetic Enzyme Sequences Predicted from the Nucleotide Sequence of the bio Operon," The Journal of Biological Chemistry, Vol. 263, p. 19577-19585, 1988.

Picciocchi A, Douce R, and Alban C, "Biochemical Characterization of the Arabidopsis Biotin Synthase Reaction. The Importance of Mitochondria in Biotin Synthesis," Plant Physiology, Vol. 127, p. 1224-1233, 2001.

Ploux O and Marquet A, "The 8-amino-7-oxopelargonate synthetase from *Bacillus sphaericus*," Biochem J., Vol. 283, p. 327-331, 1992.

Ploux O, Soularue P, Marquet A, Gloeckler R, and Lemoine Y, "Investigation of the first step of biotin biosynthesis in *Bacillus sphaericus*," Biochem. J., Vol. 287, p. 685-690, 1992.

Ploux O, Breyne O, Carillon S, and Marquet A, "Slow-binding and competitive inhibition of 8-amino-7-oxopelargonate synthase, a pyridoxal-5'-phosphate-dependent enzyme involved in biotin biosynthesis, by substrate and intermediate analogs," Eur. J. Biochem. Vol. 259, p. 63-70, 1999.

Pollock V V and Barber M J, "Kinetic and Mechanistic Properties of Biotin Sulfoxide Reductase," Biochemistry, Vol. 40, p. 1430-1440, 2001.

Rodionov D A, Mironov A A, and Gelfand M S. "Conservation of the Biotin Regulon and the BirA Regulatory Signal in Eubacteria and Archaea." Genome Research, Vol. 12, pp. 1507-1516. (2002)

Sakurai N, Akatsuka H, Kawai E, Imai Y, and Komatsubara S, "Complete sequence and organization of the *Serratia marcescens* biotin operon," Microbiology, 142: 3295-3303, 1996.

Sambrook J. and Russell D, *Molecular Cloning*, Cold Spring Harbor Laboratory Press, Cold Spring Harbor, N.Y., Vol. I, II, and III, 2001.

Weaver L H, Kwon K, Beckett D, and Matthews B W, "Competing protein:protein interactions are proposed to control the biological switch of the *E. coli* biotin repressor," Protein Science, Vol. 10, p. 2618-2622, 2001.

Webster S P, Alexeev D, Campopiano D J, Watt R M, Alexeeva M, Sawyer L, and Baxter R L, "Mechanism of 8-Amino-7-oxononanoate Synthase: Spectroscopic, Kinetic, and Crystallographic Studies," Biochemistry, Vol. 39, p. 516-528, 2000.

We claim:

1. A nucleic acid molecule comprising SEQ ID NO: 9.

2. The nucleic acid molecule of claim 1, wherein SEQ ID NO: 9 is operably linked to a nucleic acid molecule selected from the group consisting of:
   (i) SEQ ID NO: 1,
   (ii) SEQ ID NO: 5, and
   (iii) SEQ ID NO: 6.

3. An expression vector comprising SEQ ID NO: 9.

4. A recombinant host cell transformed with the expression vector of claim 3.

5. The recombinant host cell of claim 4, wherein said host cell is of genus *Pseudomonas*.

6. The recombinant host cell of claim 5, wherein said host cell is *Pseudomonas mutabilis*.

7. The recombinant host cell of claim 6, wherein said host cell produces biotin.

8. The recombinant host cell of claim 4, wherein said host cell is of genus *Escherichia*.

9. The recombinant host cell of claim 8, wherein said host cell produces biotin.

10. The recombinant host cell of claim 7, wherein said biotin-producing host cell of *Pseudomonas mutabilis* is a mutant strain that does not decrease biotin production in the presence of biotin.

11. A process for the production of biotin, the process comprising culturing the host cell of claims 7 or 9 or 10 under conditions in which biotin is produced and, optionally, isolating biotin.

12. A process for the production of biotin which process comprises culturing a biotin-expressing host cell transformed by an expression vector, which expression vector comprises SEQ ID NO: 9, in a culture medium whereby the host cell expresses biotin into the culture medium.

13. A process for the production of biotin of claim 12, wherein said host cell further comprises
    (i) SEQ ID NO: 1,
    (ii) SEQ ID NO: 5, or
    (iii) SEQ ID NO: 6.

14. The process of claim 12, wherein said process further comprises the step of:
    fermenting said culture under conditions in which biotin is produced.

15. A process for making biotin by fermentation comprising cultivating a microorganism transformed with a plasmid containing SEQ ID NO:9 whereby the transformed microorganism expresses the gene products to produce biotin.

16. The process of claim 15, wherein the microorganism is *Pseudomonas*.

17. The process of claim 15, wherein the microorganism is *Escherichia coli*.

18. The process of claim 15, wherein cultivating comprises fermenting the microorganism in the medium for a period of time at a pH of from about 6 to about 9, and at a temperature of about 30° C. to about 37° C.

19. The process of claim 18, wherein cultivating takes from about 1 to about 60 days.

20. The process of claim 18, wherein cultivating takes from about 14 to about 30 days.

21. The process of claim 18, wherein the pH is about 8.

22. The process of claim 18, wherein the temperature is from about 30° C. to 33° C.

23. The process of claim 18, wherein the amount of biotin that is produced is at least 1 gram per liter.

24. The process of claim 18, wherein the amount of biotin that is produced is at least 10 grams per liter.

\* \* \* \* \*

```
                       SEQUENCE LISTING

<160> NUMBER OF SEQ ID NOS: 16

<210> SEQ ID NO 1
<211> LENGTH: 50
<212> TYPE: DNA
<213> ORGANISM: Artificial Sequence
<220> FEATURE:
<223> OTHER INFORMATION: Artificially Synthesized Promoter Sequence
<220> FEATURE:
<221> NAME/KEY: promoter
<222> LOCATION: (1)..(50)

<400> SEQUENCE: 1
gaattcttga caattagtta actatttgtt ataatgtatt cccaagcttt             50

<210> SEQ ID NO 2
<211> LENGTH: 59
<212> TYPE: DNA
<213> ORGANISM: Artificial Sequence
<220> FEATURE:
<223> OTHER INFORMATION: Artificially Synthesized Promoter Sequence
<220> FEATURE:
<221> NAME/KEY: promoter
<222> LOCATION: (1)..(59)

<400> SEQUENCE: 2
ctagaaagct tgggaataca ttataacaaa tagttaacta attgtcaaga attctgcag    59

<210> SEQ ID NO 3
<211> LENGTH: 36
<212> TYPE: DNA
<213> ORGANISM: Artificial Sequence
<220> FEATURE:
<223> OTHER INFORMATION: Artificially Synthesized Primer Sequence

<400> SEQUENCE: 3
gacgtcactc gcatggcaac aggcctacct gattcc                            36

<210> SEQ ID NO 4
<211> LENGTH: 36
<212> TYPE: DNA
<213> ORGANISM: Artificial Sequence
<220> FEATURE:
<223> OTHER INFORMATION: Artificially Synthesized Primer Sequence

<400> SEQUENCE: 4
tctagaggtg tttcctctct acttggcttt acgaag                            36

<210> SEQ ID NO 5
<211> LENGTH: 202
<212> TYPE: DNA
<213> ORGANISM: Bacteriophage Pf1
```

```
<220> FEATURE:
<221> NAME/KEY: promoter
<222> LOCATION: (1)..(202)
<220> FEATURE:
<221> NAME/KEY: promoter
<222> LOCATION: (1)..(202)
<223> OTHER INFORMATION: G8 Promoter Sequence

<400> SEQUENCE: 5
ctgcagactc gcatggcaac aggcctacct gattccgccc gaggccgctg gatacgtgga      60
catcctggtc aacggtggtt tctccccgga agccttcggc atcggtgccg ctggcgtcct     120
gggatcgttc gtgacggggc ttttgattgg ctgggtcgcg tcacttcttc gtaaagccaa     180
gtagagagga aacacctcta ga                                              202

<210> SEQ ID NO 6
<211> LENGTH: 221
<212> TYPE: DNA
<213> ORGANISM: Bacteriophage Pf1
<220> FEATURE:
<221> NAME/KEY: promoter
<222> LOCATION: (1)..(221)
<223> OTHER INFORMATION: IR Promoter Sequence

<400> SEQUENCE: 6
ctgcagcgat tgggaattcc tcgttccggt ggcgatgggc tgggcgctgc atcactggtg      60
gtcggtgatg acggcgctag cggcggtagg ggtgccgcca tgaggggcgg ccgcgccgc     120 cggccgggag cgcaaggcat gagcgatagg ccgaaggcgc ggccgacgcc cctgtaacac    180
gtcggataac ccccgatcag caacctcata gaacctcatt a                        221

<210> SEQ ID NO 7
<211> LENGTH: 41
<212> TYPE: DNA
<213> ORGANISM: Artificial Sequence
<220> FEATURE:
<223> OTHER INFORMATION: Artificially Synthesized Primer Sequence

<400> SEQUENCE: 7
ctgcagcgat tgggaattcc tcgttccggt ggcgatgggc t                          41

<210> SEQ ID NO 8
<211> LENGTH: 43
<212> TYPE: DNA
<213> ORGANISM: Artificial Sequence
<220> FEATURE:
<223> OTHER INFORMATION: Artificially Synthesized Primer Sequence

<400> SEQUENCE: 8
tctagagttc tttacccgtt aatgaggttc tatgaggttg ctg                        43

<210> SEQ ID NO 9
<211> LENGTH: 6125
<212> TYPE: DNA
<213> ORGANISM: Artificial Sequence
<220> FEATURE:
<223> OTHER INFORMATION: Artificially Synthesized Construct

<400> SEQUENCE: 9
atgggcctta cgccgactg gatgcagcgc gacctgaacg tactctggca tccctgtacc       60
cagatgaaag accacgaacg cctgccggtg atcccgatcc gccgcggcga aggcgtctgg     120
ctggaggatt cgaaggcaa gcgctacatc gacgcggtca gttcctggtg ggtcaatgtg     180
ttcggtcacg ccaacccgcg catcaaccag cgcatcaagg accaggtcga ccagttggag    240
```

-continued

```
cacgtgatcc tcgccggatt cagccaccag ccggtgatcg agctgtcgga gcgactggtg      300
aaaatcaccc cgccggggct cgaccgggtg ttctacgccg acagcggctc ggcgggcatc      360
gaggtcgcgc tgaagatgag ctaccacttc tggctcaata gcggcaggcc gcgcaagaag      420
cgcttcgtca ccctgaccaa cagctaccac ggcgaaacca tcgcggcgat gtcggtgggc      480
gacgtggcgc tgttcaccga aacctacaag tcgctgctgc tggacaccat caaggtgccc      540
agcccggact gctttctgcg tccggacggc atgtgctggg aagaacattc gcggaacatg      600
ttcgcccaca tggagcgcac cctggccgaa gggcacgacg agatcgccgc ggtcatcgtc      660
gaaccgctga tccagggcgc cggcggcatg cgcatgtacc atccggtcta cctcaagctg      720
ctgcgcgaag cctgcgaccg ctatggcgtg cacctgatcc acgacgagat cgcggtgggc      780
ttcggccgca ccgggacgat gttcgcctgc gagcaggccg catcgccccc ggatttcctc      840
tgcctgtcca aggccctcac cggcggctac ctgccgatgt ccgcggtgct gaccagcgag      900
accatctacc ggggcttcta cgacgactac cagaccctgc gcgccttcct ccactcgcac      960
acctataccg gcaacccgct ggcctgcgcc gccgccctgg cgaccctgga catcttcgag     1020
gaagacaagg tgatcgaggc caaccgcgcg ctgtccaccc acatggccag gccaccgcg     1080 cacctggccg accacccgca tgtcgccgag gtgcgccaga ccgggatggt cctggccatc     1140
gaaatggtcc aggacaaggc gtccaggacg ccctacccct ggcaggagcg ccgcggcctg     1200
aaggtcttcc agcatggcct ggagcgcggc gcgctgctgc cccgctggg cagcgtggtg      1260 tatttcctgc cgccctacgt gattaccccg gagcagatcg acttcctcgc cgaggtggcc     1320
agcgaaggca tcgacatcgc cacccgcgac gcggtcagcg tggcggtcag cgacttccac     1380
ccggaccacc gcgatccggg ctgagagcaa ggaggctatc acatatgcac catcatcgca     1440
aggaggctat cacatatgca ccatcatcat gagtgcaacc gcttccgtcg ccacccgtca     1500
cgactggtcc ctcgccgaag tccgtgccct gttcgagcaa ccgttcaacg acctgctgtt     1560
ccaggcgcag acggtgcatc gcgcgcactt cgacccgaac cgcgtgcagg tctcgacgct     1620
gctgtcgatc aagaccggcg cctgccccga ggactgcaag tactgcccgc agtccggcca     1680
ctacaacacc ggcctggaca aggagaagct gatggaggtg cagaaggtcc tcgaggcggc     1740
ggccgaggcc aaggccatcg gttcgacccg cttctgcatg gcgctgcct ggaagcaccc      1800 gtcggccaag gacatgccct acgtcctgga gatggtcaag ggcgtgaaga agctcggcct     1860
ggagacctgc atgaccctcg gtcgcctgac ccaggaacag acccaggcgc tggcggacgc     1920
cggcctcgac tactacaacc acaacctgga tacctcgccg gagttctacg caacatcat      1980 caccacccgc acctacagcg agcgcctgca gaccctggcc tacgtgcgcg aggcggggat     2040
gaagatctgc tccggcggca tcctcggcat gggcgagtcg gtggacgacc gcgccggcct     2100
gctgatccaa ctggcgaacc tgccggagca cccggagtcg gtgccgatca acatgctggt     2160
gaaggtcaag ggcacgcccc tggcggaaga aaggacgtc gatcccttcg acttcatccg      2220
caccctggcg gtggcccgga tcatgatgcc gaagtccac gtgcgcctgt ccgcggccg      2280 cgagcagatg aacgagcaga tgcaggcgct ggccttcatg gcggggcca actcgatctt     2340 ctacggcgaa aagctgctga ccacgaagaa cccgcaggcc gaaaggaca tgcagttgtt      2400 cgcccgtctc ggcatcaagc cggaagagcg cgaagagcac gccgacgaag tgcaccaggc     2460
cgccatcgag caggcgttgg tggaacaacg cgaatcgaag ctgttctata cgccgcttc      2520 cgcctgacca tactggaagg gagggtgccg ccgtcccttc gttgcagccg ctgatgtcgg     2580
```

```
ccctgcgtgg acgggtgcgc ctgcgtccgt ccagcaacac gagcgacctg ccatgtcctt    2640
cgatctcgct tcccgcctcg ccagccggcg cgcggaagac ctctaccgcc agcggccgct    2700
gctggagtcg gcccagggcc cggacgtcgt ggtcgacggc cagccgctgc tggccttctg    2760
ttccaacgac tacctcggcc tggccaacca tcccgaggtg atcgccgcgc tgcgcgccgg    2820
cgccgagcgc tggggcgtgg gcggtggcgc ctcgcacctg gtggtcggcc acagcggccc    2880
gcaccacgaa ctggagctgg ccctcgccga attcaccggg cggccgcgcg cgctgctgtt    2940
ctccaccggc tacatggcca atctcggcgc ggtggccgcg ctggtcggca agggcgacac    3000
ggtgctggag gaccgcctca accacgcttc gctgctggat gccggattgc tctccggcgc    3060
gcgtttctcg cgctacctgc acaacgaccc ggcaagcctc gccgcgcgcc tggacaaggc    3120
cgagggcaat accctggtgg tcaccgacgg ggtcttcagc atggacggca atctcgccga    3180
cctgccggcc ctggccgccg tcgcgcaggc ccgcggcgcc tggctgatgg tcgacgacgc    3240
gcatggcttc ggcccgctgg gcgccagcgg cggcgggatc gtcgaacact tcggcctcgg    3300
ccaggagcag gtgccggtgc tgatcggcac cctcggcaag ggtttcggta ccgccggcgc    3360
cttcgtagcg ggcagcgagg aactgatcga gaccctgatc cagtacgccc ggccctacat    3420
ctacaccacc agccagccgc cagcggtggc ctgcgccacc ctgaagagcc tggagctgct    3480
gcgccgcgaa agctggcggc ggcaacacct ggcggcgctg atcgcccgtt ccgccatgg    3540 cgccgaggcg cttggcctga ccctgatgga cagcttcacg ccgatccagc cgatcctggt    3600
cggcggcagc cgccaggccg tggccctggc cggcatgctt cgagcccgtg gcatcatggt    3660
cggcgcgatc cgcccgccaa ccgtgccggc caacagcgcg cggctgcgcg tcacgctgtc    3720
cgccgcgcac agcgaagcgc aggtcgaccg cttgctcgaa gccctcggcg aaagctggcg    3780
acagctgtcg tctagccttc tggcagagat cgaagccgag gagggagacg atgcgtgacc    3840
acttgatcct gttgccgggc tggggcctgg gtagcgcacc gctggaaccg ctgcgcgacg    3900
cgctgcacga gcgcgagccg cacctgaacg tgttgatcga gccgctgccg tcgctggacg    3960
acgccgccga ctggctcgac gaactcgacg ataacctgcc gcgcgatagc tggctggccg    4020
gctggtcgct gggaggcatg ctcgccggcg aactggcggc gcgccgcggc gacgattgcc    4080
ggggactgct gaccctggcc agcaatccgt gcttccgcgt gcgcgaggac tggccgaacg    4140
cgatgccggc ggaaaccttc gaggacttct tcgaggcttt cctgctcgaa ccgcacctga    4200
cccgcaagcg tttcaccctg ctggtcagcc agggtgcgcg cgaccctcgg accctggcgc    4260
ggcaactgca ggtggcgctg ccgcagctgg agcgcgaggc gctggtcgcc ggcctgcagt    4320
tgctcggcca actggatacc cgggccgccc tggaaaactt ccgcgggccg caattgcacc    4380
tgttcgccga agccgatgcg ctggtgccgc tggccgccgc cgaggccctg ctcgagtggc    4440
tgccggacgt cgaggtctcg accctggcgg ccagtcacgg cctgccgctg aatgcccgg    4500 acgaggtggc cggcgcaatc ctgagattcc ttcgcgaggg tgacgatgcc tgacgattcc    4560
tcgccgctgc tggcgcccca tggcgttgcc gcgctgcccg acaagcgcca ggtcgccgcg    4620 tcgtttttccc gcgcggcggc cagctacgac gcggtgccgc aactccagcg cggcgtcggt    4680
gagagcctgc tgtcggcatt gccggaaggc ttctcgccgc gccgctgggt cgatctcggc    4740
tgcggcaccg gttatttcag ccgggccctg gaacgacgct tcggtgcggc cgagggcctg    4800
gccgtggata tcgccgaagg catgctgcgg catgcccgag cgcgcggcgg cgccagccat    4860
ttcatcggcg cgacgccga gaggctgccg ttgcgcgacg gcagttgcga cctgctgttc    4920
tccagcctgg ccatccagtg ggtcgccgac ctcccggcgg tcctggccga ggcgcggcgg    4980
```

-continued

| | |
|---|---|
| gtcctgcggc cgggcggcgt gctggcgttc agcagcctgt gcgtcggtac cctgggcgag | 5040 |
| ttgcgcgaca gttggcgggt ggtggacggc ttcgtccacg tcaatcgctt ccgcgccttc | 5100 |
| gccgactacc tgcaacacgc ggccggcagc ggcctgctgc cgctgaccct gcgccacgag | 5160 |
| gaccggctcc tgcatttccc cgacctgcgc agcctgaccc acgaactcaa ggcgctgggc | 5220 |
| gcgcacaacc tcaaccccgg gcggcccgac ggcctgaccg ggcgccagcg catccgcgcg | 5280 |
| ctggtcgccg cctacgagcg tttccgccag cccgaggggc tgcccgctac ctaccgcgtc | 5340 |
| gtcttcggcg tgctgcgcaa ggattcctga accatgccgg cgttcttcgt caccggtacc | 5400 |
| gacaccgaga tcggcaagac caccatcgcc gccggcctgc tccacgcggc ccggagtgcc | 5460 |
| ggcctgagca ccgccgcggc gaagccggtg gcctccggct gcgagcccac ggcgcaaggc | 5520 |
| ctgcgcaatg cgacgcgtt ggtgttgctc ggccagtgct cgctggcgct ggcctacgag | 5580 |
| caggtcaacc cgctggcctt cgcaccggcc atcgccccgc acctggcggc gcgcgaggct | 5640 |
| ggcgtcgaac tgagcgccgc acgcttgcac gaggcggtgc gcgaggtgct ggcgctacag | 5700 |
| gccgacttca ccctggtgga gggcgccggc ggatggcgcg tgccgttgct gggccgcgag | 5760 |
| aacctgtccg acctggcgcg cctgctggcg ctgccggtgg tgctggtggt cggcgtgcgc | 5820 |
| ctgggctgta tcaaccatgc gctgctcagc gccgaggcga tcctgggcga cggcctggcg | 5880 |
| ctggccggct gggtggccaa cgtcgtcgac ccggctacct cgcgcctgga agagaacctg | 5940 |
| gcgaccctcg ccgaacgcct gccggcgccc tgcctgggtc gggtaccgcg cctggaggaa | 6000 |
| gccactcccg cggccgtggc cgcgcacctc gacctgcggc ccctgggtat cgggctataa | 6060 |
| acagcgggcc gtccataacc aacgggcggt acccagcgcc ggccaagtct gcttgaatag | 6120 |
| aagcc | 6125 |

<210> SEQ ID NO 10
<211> LENGTH: 46
<212> TYPE: DNA
<213> ORGANISM: Artificial Sequence
<220> FEATURE:
<223> OTHER INFORMATION: Artificially Synthesized Primer Sequence

<400> SEQUENCE: 10

| | |
|---|---|
| gacgacgaca agatgagtgc aaccgcttcc gtcgccaccc gtcacg | 46 |

<210> SEQ ID NO 11
<211> LENGTH: 51
<212> TYPE: DNA
<213> ORGANISM: Artificial Sequence
<220> FEATURE:
<223> OTHER INFORMATION: Artificially Synthesized Primer Sequence

<400> SEQUENCE: 11

| | |
|---|---|
| gaggagaagc ccggttttat agcccgatac ccaggggccg caggtcgagg t | 51 |

<210> SEQ ID NO 12
<211> LENGTH: 4698
<212> TYPE: DNA
<213> ORGANISM: Pseudomonas aeruginosa

<400> SEQUENCE: 12

| | |
|---|---|
| caccatcatc gcaaggaggc tatcacatat gcaccatcat catgagtgca accgcttccg | 60 |
| tcgccacccg tcacgactgg tccctcgccg aagtccgtgc cctgttcgag caaccgttca | 120 |
| acgacctgct gttccaggcg cagacggtgc atcgcgcgca cttcgacccg aaccgcgtgc | 180 |

-continued

```
aggtctcgac gctgctgtcg atcaagaccg gcgcctgccc cgaggactgc aagtactgcc    240
cgcagtccgg ccactacaac accggcctgg acaaggagaa gctgatggag gtgcagaagg    300
tcctcgaggc ggcggccgag gccaaggcca tcggttcgac ccgcttctgc atgggcgctg    360
cctggaagca cccgtcggcc aaggacatgc cctacgtcct ggagatggtc aagggcgtga    420
agaagctcgg cctggagacc tgcatgaccc tcggtcgcct gacccaggaa cagacccagg    480
cgctggcgga cgccggcctc gactactaca accacaacct ggatacctcg ccggagttct    540
acggcaacat catcaccacc cgcacctaca gcgagcgcct gcagaccctg cctacgtgc     600 gcgaggcggg gatgaagatc tgctccggcg gcatcctcgg catgggcgag tcggtggacg    660
accgcgccgg cctgctgatc caactggcga acctgccgga gcacccggag tcggtgccga    720
tcaacatgct ggtgaaggtc aagggcacgc ccctggcgga agagaaggac gtcgatccct    780
tcgacttcat ccgcaccctg gcggtggccc ggatcatgat gccgaagtcc cacgtgcgcc    840
tgtccgccgg ccgcgagcag atgaacgagc agatgcaggc gctggccttc atggccgggg    900
ccaactcgat cttctacggc gaaaagctgc tgaccacgaa gaacccgcag gccgaaaagg    960
acatgcagtt gttcgcccgt ctcggcatca agcggaaga gcgcgaagag cacgccgacg    1020
aagtgcacca ggccgccatc gagcaggcgt tggtggaaca acgcgaatcg aagctgttct    1080
ataacgccgc ttccgcctga ccatactgga agggagggtg ccgccgtccc ttcgttgcag    1140
ccgctgatgt cggccctgcg tggacgggtg cgcctgcgtc cgtccagcaa cacgagcgac    1200
ctgccatgtc cttcgatctc gcttcccgcc tcgccagccg gcgcgcggaa gacctctacc    1260
gccagcggcc gctgctggag tcggcccagg gcccggacgt cgtggtcgac ggccagccgc    1320
tgctggcctt ctgttccaac gactacctcg gcctggccaa ccatcccgag gtgatcgccg    1380
cgctgcgcgc cggcgccgag cgctggggcg tgggcggtgg cgcctcgcac ctggtggtcg    1440
gccacagcgg cccgcaccac gaactggagc tggccctcgc cgaattcacc gggcggccgc    1500
gcgcgctgct gttctccacc ggctacatgg ccaatctcgg cgcggtggcc gcgctggtcg    1560
gcaagggcga cacggtgctg gaggaccgcc tcaaccacgc ttcgctgctg gatgccggat    1620
tgctctccgg cgcgcgtttc tcgcgctacc tgcacaacga cccggcaagc ctcgccgcgc    1680
gcctggacaa ggccgagggc aatacccctgg tggtcaccga cggggtcttc agcatggacg    1740
gcaatctcgc cgacctgccg gccctggccg ccgtcgcgca ggcccgcggc gcctggctga    1800
tggtcgacga cgcgcatggc ttcggcccgc tgggcgccag cggcggcggg atcgtcgaac    1860
acttcggcct cggccaggag caggtgccgg tgctgatcgg caccctcggc aagggttcg     1920 gtaccgccgg cgccttcgta gcgggcagcg aggaactgat cgagaccctg atccagtacg    1980
cccggcccta catctacacc accagccagc cgccagcggt ggcctgcgcc accctgaaga    2040
gcctggagct gctgcgccgc gaaagctggc ggcggcaaca cctggcggcg ctgatcgccc    2100
gtttccgcca tggcgccgag gcgcttggcc tgacccgat ggacagcttc acgccgatcc     2160
agccgatcct ggtcggcggc agccgccagg ccgtggccct ggccggcatg cttcgagccc    2220
gtggcatcat ggtcggcgcg atccgcccgc caaccgtgcc ggccaacagc gcgcggctgc    2280
gcgtcacgct gtccgccgcg cacagcgaag cgcaggtcga ccgcttgctc gaagccctcg    2340
gcgaaagctg gcgacagctg tcgtctagcc ttctggcaga gatcgaagcc gaggaggag     2400 acgatgcgtg accacttgat cctgttgccg ggctgggcc tgggtagcgc accgctggaa     2460
ccgctgcgcg acgcgctgca cgagcgcgag ccgcacctga acgtgttgat cgagccgctg    2520
ccgtcgctgg acgacgccgc cgactggctc gacgaactcg acgataacct gccgcgcgat    2580
```

```
agctggctgg ccggctggtc gctgggaggc atgctcgccg cgaactggcg ggcgcgccgc   2640
ggcgacgatt gccggggact gctgaccctg ccagcaatc cgtgcttccg cgtgcgcgag    2700
gactggccga acgcgatgcc ggcggaaacc ttcgaggact cttcgaggc tttcctgctc    2760
gaaccgcacc tgaccgcaa gcgtttcacc ctgctggtca gccagggtgc gcgcgaccct    2820
cggaccctgg cgcggcaact gcaggtggcg ctgccgcagc tggagcgcga ggcgctggtc   2880
gccggcctgc agttgctcgg ccaactggat accgggccg ccctggaaaa cttccgcggg    2940
ccgcaattgc acctgttcgc cgaagccgat gcgctggtgc cgctgccgc cgccgaggcc    3000
ctgctcgagt ggctgccgga cgtcgaggtc tcgaccctgg cggccagtca cggcctgccg   3060
ctggaatgcc cggacgaggt ggccggcgca atcctgagat ccttcgcga gggtgacgat    3120
gcctgacgat tcctcgccgc tgctggcgcc ccatggcgtt gccgcgctgc cgacaagcg    3180
ccaggtcgcc cgtcgttttt cccgcgcggc ggccagctac gacgcggtgg ccgaactcca   3240
gcgcggcgtc ggtgagagcc tgctgtcggc attgccggaa ggcttctcgc cgcgccgctg   3300
ggtcgatctc ggctgcggca ccggttattt cagcccgggcc ctggaacgac gcttcggtgc  3360
ggccgagggc ctgccgtgg atatcgccga aggcatgctg cggcatgccc gagcgcgcgg   3420
cggcgccagc catttcatcg gcggcgacgc cgagaggctg ccgttgcgcg acggcagttg   3480
cgacctgctg ttctccagcc tggccatcca gtggtgcgcc gacctccgg cggtcctggc   3540
cgaggcgcgg cgggtcctgc ggccgggcgg cgtgctggcg ttcagcagcc tgtgcgtcgg   3600
taccctgggc gagttgcgcg acagttggcg ggtggtggac ggcttcgtcc acgtcaatcg   3660
cttccgcgcc ttcgccgact acctgcaaca cgcggccggc agcggcctgc tgccgctgac   3720
cctgcgccac gaggaccggc tcctgcattt ccccgacctg cgcagcctga cccacgaact   3780
caaggcgctg ggcgcgcaca acctcaaccc cgggcggccc gacggcctga ccgggcgcca   3840
gcgcatccgc gcgctggtcg ccgcctacga gcgtttccgc cagcccgagg gctgccccgc   3900
tacctaccgc gtcgtcttcg gcgtgctgcg caaggattcc tgaaccatgc cggcgttctt   3960
cgtcaccggt accgacaccg agatcggcaa gaccaccatc gccgccggcc tgctccacgc   4020
ggcccggagt gccggcctga gcaccgccgc ggcgaagccg gtggcctccg gctgcgagcc   4080
cacggcgcaa ggcctgcgca atggcgacgc gttggtgttg ctcggccagt gctcgctggc   4140
gctggcctac gagcaggtca acccgctggc cttcgcaccg gccatcgccc cgcacctggc   4200
ggcgcgcgag gctggcgtcg aactgagcgc cgcacgcttg cacgaggcgg tgcgcgaggt   4260
gctggcgcta caggccgact tcaccctggt ggagggcgcc ggcggatggc gcgtgccgtt   4320
gctgggccgc gagaacctgt ccgacctggc gcgcctgctg gcgctgccgg tggtgctggt   4380
ggtcggcgtg cgcctgggct gtatcaacca tgcgctgctc agcgccgagg cgatcctggg   4440
cgacggcctg cgcgctggcg gctggtggc caacgtcgtc gacccggcta cctcgcgcct   4500
ggaagagaac ctggcgaccc tcgccgaacg cctgccggcg ccctgcctgg gtcgggtacc   4560
gcgcctggag gaagccactc ccgcggccgt ggcgcgcac ctcgacctgc ggcccctggg    4620
tatcgggcta taaacagcgg gccgtccata accaacgggc ggtacccagc gccggccaag   4680
tctgcttgaa tagaagcc                                                 4698
```

<210> SEQ ID NO 13
<211> LENGTH: 1427
<212> TYPE: DNA
<213> ORGANISM: Pseudomonas aeruginosa

```
<400> SEQUENCE: 13
atgggcctta acgccgactg gatgcagcgc gacctgaacg tactctggca tccctgtacc      60
cagatgaaag accacgaacg cctgccggtg atcccgatcc gccgcggcga aggcgtctgg     120
ctggaggatt tcgaaggcaa agcgctacatc gacgcggtca gttcctggtg ggtcaatgtg     180
ttcggtcacg ccaacccgcg catcaaccag cgcatcaagg accaggtcga ccagttggag     240
cacgtgatcc tcgccggatt cagccaccag ccggtgatcg agctgtcgga gcgactggtg     300
aaaatcaccc cgccggggct cgaccggtg ttctacgccg acagcggctc ggcgggcatc      360
gaggtcgcgc tgaagatgag ctaccacttc tggctcaata gcggcaggcc gcgcaagaag     420
cgcttcgtca ccctgaccaa cagctaccac ggcgaaacca tcgcggcgat gtcggtgggc     480
gacgtggcgc tgttcaccga acctacaag tcgctgctgc tggacaccat caaggtgccc      540
agcccggact gctttctgcg tccggacggc atgtgctggg aagaacattc gcggaacatg     600
ttcgcccaca tggagcgcac cctggccgaa gggcacgacg agatcgccgc ggtcatcgtc     660
gaaccgctga tccagggcgc cggcggcatg cgcatgtacc atccggtcta cctcaagctg     720
ctgcgcgaag cctgcgaccg ctatggcgtg cacctgatcc acgacgagat cgcggtgggc     780
ttcggccgca ccgggacgat gttcgcctgc gagcaggccg gcatcgcccc ggatttcctc     840
tgcctgtcca aggccctcac cggcggctac ctgccgatgt ccgcggtgct gaccagcgag     900
accatctacc ggggcttcta cgacgactac cagaccctgc gcgccttcct ccactcgcac     960
acctataccg gcaacccgct ggcctgcgcc gccgcctgg cgaccctgga catcttcgag      1020
gaagacaagg tgatcgaggc caaccgcgcg ctgtccaccc acatggccag ggccaccgcg     1080
cacctggccg accacccgca tgtcgccgag gtgcgccaga ccgggatggt cctggccatc     1140
gaaatggtcc aggacaaggc gtccaggacg ccctacccct ggcaggagcg ccgcggcctg     1200
aaggtcttcc agcatggcct ggagcgcggc gcgctgctgc cccgctggg cagcgtggtg      1260 tatttcctgc cgccctacgt gattaccccg gagcagatcg acttcctcgc cgaggtggcc     1320
agcgaaggca tcgacatcgc cacccgcgac gcggtcagcg tggcggtcag cgacttccac     1380
ccggaccacc gcgatccggg ctgagagcaa ggaggctatc acatatg                   1427

<210> SEQ ID NO 14
<211> LENGTH: 77
<212> TYPE: DNA
<213> ORGANISM: Artificial Sequence
<220> FEATURE:
<223> OTHER INFORMATION: Artificially Synthesized Primer Sequence

<400> SEQUENCE: 14 tccccctctag aaataatttt gtttaacttt aagaaggaga tataccatgg gccttaacgc     60
cgactggatg cagcgcg                                                     77

<210> SEQ ID NO 15
<211> LENGTH: 49
<212> TYPE: DNA
<213> ORGANISM: Artificial Sequence
<220> FEATURE:
<223> OTHER INFORMATION: Artificially Synthesized Primer Sequence

<400> SEQUENCE: 15
gatgatggtg catatgtgat agcctccttg ctcagcccgg atcgcggtg                  49

<210> SEQ ID NO 16
<211> LENGTH: 6346
```

<212> TYPE: DNA
<213> ORGANISM: Artificial Sequence
<220> FEATURE:
<223> OTHER INFORMATION: Artificially Synthesized Construct with the
       IR Promoter

<400> SEQUENCE: 16

```
ctgcagcgat tgggaattcc tcgttccggt ggcgatgggc tgggcgctgc atcactggtg      60
gtcggtgatg acggcgctag cggcggtagg ggtgccgcca tgaggggcgg gccgcgccgc     120
cggccgggag cgcaaggcat gagcgatagg ccgaaggcgc ggccgacgcc cctgtaacac     180
gtcggataac ccccgatcag caacctcata gaacctcatt aatgggcctt aacgccgact     240
ggatgcagcg cgacctgaac gtactctggc atccctgtac ccagatgaaa gaccacgaac     300
gcctgccggt gatcccgatc cgccgcgcg aaggcgtctg gctggaggat ttcgaaggca      360
agcgctacat cgacgcggtc agttcctggt gggtcaatgt gttcggtcac gccaacccgc     420
gcatcaacca gcgcatcaag gaccaggtcg accagttgga gcacgtgatc ctcgccggat     480
tcagccacca gccggtgatc gagctgtcgg agcgactggt gaaaatcacc ccgccggggc     540
tcgaccgggt gttctacgcc gacagcggct cggcgggcat cgaggtcgcg ctgaagatga     600
gctaccactt ctggctcaat agcggcaggc cgcgcaagaa gcgcttcgtc accctgacca     660
acagctacca cggcgaaacc atcgcggcga tgtcggtggg cgacgtggcg ctgttcaccg     720
aaacctacaa gtcgctgctg ctggacacca tcaaggtgcc cagcccggac tgctttctgc     780
gtccggacgg catgtgctgg gaagaacatt gcgggaacat gttcgcccac atggagcgca     840
ccctggccga agggcacgac gagatcgccg cggtcatcgt cgaaccgctg atccagggcg     900
ccggcggcat gcgcatgtac catccggtct acctcaagct gctgcgcgaa gcctgcgacc     960
gctatggcgt gcacctgatc cacgacgaga tcgcggtggg cttcggccgc accgggacga    1020
tgttcgcctg cgagcaggcc ggcatcgccc cggatttcct ctgcctgtcc aaggccctca    1080
ccggcggcta cctgccgatg tccgcggtgc tgaccagcga gaccatctac cggggcttct    1140
acgacgacta ccagaccctg cgcgccttcc tccactcgca cacctatacc ggcaacccgc    1200
tggcctgcgc cgccgccctg gcgaccctgg acatcttcga ggaagacaag gtgatcgagg    1260
ccaaccgcgc gctgtccacc cacatggcca gggccaccgc gcacctggcc gaccaccgc     1320
atgtcgccga ggtgcgccag accgggatgg tcctggccat cgaaatggtc caggacaagg    1380
cgtccaggac gccctacccc tgcaggagc cgcgggcct gaaggtcttc cagcatggcc      1440
tggagcgcgg cgcgctgctg cgcccgctgg gcagcgtggt gtatttcctg ccgccctacg    1500
tgattacccc ggagcagatc gacttcctcg ccgaggtggc cagcgaaggc atcgacatcg    1560
ccacccgcga cgcggtcagc gtggcggtca gcgacttcca cccggaccac gcgatccgg    1620
gctgagagca aggaggctat cacatatgca ccatcatcgc aaggaggcta tcacatatgc    1680
accatcatca tgagtgcaac cgcttccgtc gccacccgtc acgactggtc cctcgccgaa    1740
gtccgtgccc tgttcgagca accgttcaac gacctgctgt ccaggcgca gacggtgcat    1800
cgcgcgcact tcgacccgaa ccgcgtgcag gtctcgacgc tgctgtcgat caagaccggc    1860
gcctgccccg aggactgcaa gtactgcccg cagtccggcc actacaacac cggcctggac    1920
aaggagaagc tgatggaggt gcagaaggtc ctcgaggcgg cggccgaggc caaggccatc    1980
ggttcgaccc gcttctgcat gggcgctgcc tggaagcacc cgtcggccaa ggacatgccc    2040
tacgtcctgg agatggtcaa gggcgtgaag aagctcggcc tggagacctg catgaccctc    2100
ggtcgcctga cccaggaaca gacccaggcg ctggcggacg ccggcctcga ctactacaac    2160
```

-continued

```
cacaacctgg atacctcgcc ggagttctac ggcaacatca tcaccacccg cacctacagc    2220
gagcgcctgc agaccctggc ctacgtgcgc gaggcgggga tgaagatctg ctccggcggc    2280
atcctcggca tgggcgagtc ggtggacgac cgcgccggcc tgctgatcca actggcgaac    2340
ctgccggagc acccggagtc ggtgccgatc aacatgctgg tgaaggtcaa gggcacgccc    2400
ctggcggaag agaaggacgt cgatcccttc gacttcatcc gcaccctggc ggtgccccgg    2460
atcatgatgc cgaagtccca cgtgcgcctg tccgccggcc gcgagcagat gaacgagcag    2520
atgcaggcgc tggccttcat ggccggggcc aactcgatct tctacggcga aaagctgctg    2580
accacgaaga acccgcaggc cgaaaaggac atgcagttgt tcgcccgtct cggcatcaag    2640
ccggaagagc gcgaagagca cgccgacgaa gtgcaccagg ccgccatcga gcaggcgttg    2700
gtggaacaac gcgaatcgaa gctgttctat aacgccgctt ccgcctgacc atactggaag    2760
ggagggtgcc gccgtccctt cgttgcagcc gctgatgtcg gccctgcgtg gacgggtgcg    2820
cctgcgtccg tccagcaaca cgagcgacct gccatgtcct tcgatctcgc ttcccgcctc    2880
gccagccggc gcgcggaaga cctctaccgc cagcggccgc tgctggagtc ggcccagggc    2940
ccggacgtcg tggtcgacgg ccagccgctg ctggccttct gttccaacga ctacctcggc    3000
ctggccaacc atcccgaggt gatcgccgcg ctgcgcgccg gcgccgagcg ctggggcgtg    3060
ggcggtggcg cctcgcacct ggtggtcggc cacagcggcc gcaccacga  actgagctg     3120 gccctcgccg aattcaccgg gcggccgcgc gcgctgctgt tctccaccgg ctacatggcc    3180
aatctcggcc cggtggccgc gctggtcggc aagggcgaca cggtgctgga ggaccgcctc    3240
aaccacgctt cgctgctgga tgccggattg ctctccggcg cgcgtttctc gcgctacctg    3300
cacaacgacc cggcaagcct cgccgcgcgc ctggacaagg ccgagggcaa taccctggtg    3360
gtcaccgacg gggtcttcag catggacggc aatctcgccg acctgccggc cctggccgcc    3420
gtcgcgcagg cccgcggcgc ctggctgatg tcgacgacg  cgcatggctt cggcccgctg    3480
ggcgccagcg gcggcgggat cgtcgaacac ttcggcctcg gccaggagca ggtgccggtg    3540
ctgatcggca ccctcggcaa gggtttcggt accgccggcg ccttcgtagc gggcagcgag    3600
gaactgatcg agaccctgat ccagtacgcc cggccctaca tctacaccac cagccagccg    3660
ccagcggtgg cctgcgccac cctgaagagc ctggagctgc tgcgccgcga aagctggcgg    3720
cggcaacacc tggcggcgct gatcgcccgt ttccgccatg gcgccgaggc gcttggcctg    3780
accctgatgg acagcttcac gccgatccag ccgatcctgg tcggcggcag ccgccaggcc    3840
gtggccctgg ccggcatgct tcgagcccgt ggcatcatgg tcggcgcgat ccgcccgcca    3900
accgtgccgg ccaacagcgc gcggctgcgc gtcacgctgt ccgccgcgca cagcgaagcg    3960
caggtcgacc gcttgctcga agccctcggc gaaagctggc gacagctgtc gtctagcctt    4020
ctggcagaga tcgaagccga ggagggagac gatgcgtgac cacttgatcc tgttgccggg    4080
ctggggcctg ggtagcgcac cgctggaacc gctgcgcgac gcgctgcacg agcgcgagcc    4140
gcacctgaac gtgttgatcg agccgctgcc gtcgctggac gacgccgccg actggctcga    4200
cgaactcgac gataacctgc cgcgcgatag ctggctggcc ggctggtcgc tgggaggcat    4260
gctcgccggc gaactggcgg cgccgccgcg cgacgattgc cggggactgc tgaccctggc    4320
cagcaatccg tgcttccgcg tgcgcgagga ctggccgaac gcgatgccgg cggaaacctt    4380
cgaggacttc ttcgaggctt tcctgctcga accgcacctg acccgcaagc gtttcaccct    4440
gctggtcagc cagggtgcgc gcgacccccg accctggcg  cggcaactgc aggtggcgct    4500
```

```
gccgcagctg gagcgcgagg cgctggtcgc cggcctgcag ttgctcggcc aactggatac    4560
ccgggccgcc ctggaaaact tccgcgggcc gcaattgcac ctgttcgccg aagccgatgc    4620
gctggtgccg ctggccgccg ccgaggcct gctcgagtgg ctgccggacg tcgaggtctc     4680
gaccctggcg gccagtcacg gcctgccgct ggaatgcccg gacgaggtgg ccggcgcaat    4740
cctgagattc cttcgcgagg gtgacgatgc ctgacgattc ctcgccgctg ctggcgcccc    4800
atggcgttgc cgcgctgccc gacaagcgcc aggtcgccgc gtcgttttcc cgcgcggcgg    4860
ccagctacga cgcggtggcc gaactccagc gcggcgtcgg tgagagcctg ctgtcggcat    4920
tgccggaagg cttctcgccg cgccgctggg tcgatctcgg ctgcggcacc ggttatttca    4980
gccgggccct ggaacgacgc ttcggtgcgg ccgagggcct ggccgtggat atcgccgaag    5040
gcatgctgcg gcatgcccga gcgcgcggcg gcgccagcca tttcatcggc ggcgacgccg    5100
agaggctgcc gttgcgcgac ggcagttgcg acctgctgtt ctccagcctg gccatccagt    5160
ggtgcgccga cctcccggcg gtcctggccg aggcgcggcg ggtcctgcgg ccgggcggcg    5220
tgctggcgtt cagcagcctg tgcgtcggta ccctgggcga gttgcgcgac agttggcggg    5280
tggtggacgg cttcgtccac gtcaatcgct tccgcgcctt cgccgactac ctgcaacacg    5340
cggccggcag cggcctgctg ccgctgaccc tgcgccacga ggaccggctc ctgcatttcc    5400
ccgacctgcg cagcctgacc cacgaactca aggcgctggg cgcgcacaac ctcaaccccg    5460
ggcggcccga cggcctgacc gggcgccagc gcatccgcgc gctggtcgcc gcctacgagc    5520
gtttccgcca gcccgagggg ctgccgcta cctaccgcgt cgtcttcggc gtgctgcgca     5580
aggattcctg aaccatgccg gcgttcttcg tcaccggtac cgacaccgag atcggcaaga    5640
ccaccatcgc cgccggcctg ctccacgcgg cccggagtgc cggcctgagc accgccgcgg    5700
cgaagccggt ggcctccggc tgcgagccca cggcgcaagg cctgcgcaat ggcgacgcgt    5760
tggtgttgct cggccagtgc tcgctggcgc tggcctacga gcaggtcaac ccgctggcct    5820
tcgcaccggc catcgccccg cacctggcgg cgcgcgaggc tggcgtcgaa ctgagcgccg    5880
cacgcttgca cgaggcggtg cgcgaggtgc tggcgctaca ggccgacttc accctggtgg    5940
agggcgccgg cggatggcgc gtgccgttgc tgggccgcga gaacctgtcc gacctggcgc    6000
gcctgctggc gctgccggtg gtgctggtgg tcggcgtgcg cctgggctgt atcaaccatg    6060
cgctgctcag cgccgaggcg atcctgggcg acggcctggc gctggccggc tgggtggcca    6120
acgtcgtcga cccggctacc tcgcgcctgg aagagaacct ggcgaccctc gccgaacgcc    6180
tgccggcgcc ctgcctgggt cgggtaccgc gcctggagga agccactccc gcggccgtgg    6240
ccgcgcacct cgacctgcgg cccctgggta tcgggctata acagcgggc cgtccataac     6300
caacgggcgg tacccagcgc cggccaagtc tgcttgaata gaagcc                   6346
```